United States Patent
He et al.

(10) Patent No.: US 12,211,240 B2
(45) Date of Patent: Jan. 28, 2025

(54) APPARATUSES, SYSTEMS, AND METHODS FOR MANAGING AUTO-EXPOSURE OF IMAGE FRAMES BASED ON SIGNAL REGION SIZE

(71) Applicant: Intuitive Surgical Operations, Inc., Sunnyvale, CA (US)

(72) Inventors: Zhen He, Cupertino, CA (US); Jeffrey M. DiCarlo, Austin, TX (US); Max J. Trejo, San Jose, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 850 days.

(21) Appl. No.: 17/369,660

(22) Filed: Jul. 7, 2021

(65) Prior Publication Data
US 2022/0014661 A1    Jan. 13, 2022

Related U.S. Application Data

(60) Provisional application No. 63/050,563, filed on Jul. 10, 2020.

(51) Int. Cl.
| | | |
|---|---|---|
| *A61B 90/00* | (2016.01) | |
| *G06V 10/141* | (2022.01) | |
| *G06V 10/22* | (2022.01) | |
| *H04N 23/72* | (2023.01) | |

(52) U.S. Cl.
CPC .......... *G06V 10/141* (2022.01); *A61B 90/37* (2016.02); *G06V 10/22* (2022.01); *H04N 23/72* (2023.01); *A61B 2090/376* (2016.02)

(58) Field of Classification Search
None
See application file for complete search history.

(56) References Cited

U.S. PATENT DOCUMENTS

| 9,313,415 B2 | 4/2016 | Schieltz |
| 2015/0216398 A1* | 8/2015 | Yang .................. A61B 1/00172 600/109 |
| 2021/0110190 A1 | 4/2021 | Park et al. |
| 2021/0258465 A1* | 8/2021 | Saito ...................... H04N 23/60 |

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

*Primary Examiner* — Hoon K Song

(57) ABSTRACT

An illustrative apparatus may identify, within an image frame captured by an image capture system, a signal region that includes pixels having auto-exposure values exceeding an auto-exposure value threshold. The apparatus may adjust, based on the auto-exposure values of the pixels included within the signal region, one or more auto-exposure parameters used by the image capture system to capture an additional image frame. Additionally, the apparatus may determine, based on a size of the signal region within the image frame, whether to change the auto-exposure value threshold. Corresponding apparatuses, systems, and methods for managing auto-exposure of image frames are also disclosed.

20 Claims, 11 Drawing Sheets

APPARATUSES, SYSTEMS, AND METHODS FOR MANAGING AUTO-EXPOSURE OF IMAGE FRAMES BASED ON SIGNAL REGION SIZE

RELATED APPLICATIONS

The present application also claims priority under 35 U.S.C. § 119(e) to U.S. Provisional Patent Application No. 63/050,563, filed Jul. 10, 2020, which application is incorporated herein by reference in its entirety.

BACKGROUND INFORMATION

Auto-exposure algorithms operate by determining how much light is present in a scene based on an analysis of image frames depicting the scene, and adjusting auto-exposure parameters of an image capture device capturing the image frames. In this manner, the auto-exposure parameters may be continuously set to cause the image capture device to provide a desired amount of exposure for image frames being captured. Without good auto-exposure management, detail may be lost during the image capture process by either over-exposure (e.g., where details are lost because of saturation and the image looks too bright) or under-exposure (e.g., where details are lost because of noise and the image looking too dark).

While conventional auto-exposure algorithms adequately serve many types of images, images depicting content against a darkened background may present particular challenges, such as when the content is not very bright. For instance, in attempting to capture image frames in a manner that reduces noise, a conventional auto-exposure algorithm may adjust auto-exposure parameters so as to overexpose or underexpose content that a viewer may desire to see.

SUMMARY

The following description presents a simplified summary of one or more aspects of the apparatuses, systems, and methods described herein. This summary is not an extensive overview of all contemplated aspects and is intended to neither identify key or critical elements of all aspects nor delineate the scope of any or all aspects. Its sole purpose is to present one or more aspects of the systems and methods described herein as a prelude to the detailed description that is presented below.

An illustrative apparatus for managing auto-exposure of image frames may include one or more processors and memory storing executable instructions that, when executed by the one or more processors, cause the apparatus to perform various operations described herein. For example, the apparatus may identify, within an image frame captured by an image capture system, a signal region that includes pixels having auto-exposure values exceeding an auto-exposure value threshold. Based on the auto-exposure values of the pixels included within the signal region, the apparatus may adjust one or more auto-exposure parameters used by the image capture system to capture an additional image frame. Additionally, based on a size of the signal region within the image frame, the apparatus may determine whether to change the auto-exposure value threshold.

An illustrative system for managing auto-exposure of image frames may include a fluorescence illumination source, an image capture device, and one or more processors. The fluorescence illumination source may be configured to illuminate tissue that includes a fluorescence imaging agent that fluoresces when illuminated by the fluorescence illumination source. The image capture device may be configured to capture an image frame sequence that includes an image frame depicting the tissue as illuminated by the fluorescence illumination source. The one or more processors may be configured to identify, within the image frame captured by the image capture system, a signal region that includes pixels having auto-exposure values exceeding an auto-exposure value threshold. Based on the auto-exposure values of the pixels included within the signal region, the one or more processors may adjust one or more auto-exposure parameters used by the image capture system to capture an additional image frame of the image frame sequence. Additionally, based on a size of the signal region within the image frame, the one or more processors may determine whether to change the auto-exposure value threshold.

An illustrative non-transitory computer-readable medium may store instructions that, when executed, cause one or more processors of a computing device to perform various operations described herein. For example, the one or more processors may identify, within an image frame captured by an image capture system, a signal region that includes pixels having auto-exposure values exceeding an auto-exposure value threshold. Based on the auto-exposure values of the pixels included within the signal region and based on auto-exposure targets of the pixels included within the signal region, the apparatus may adjust one or more auto-exposure parameters used by the image capture system to capture an additional image frame. Additionally, based on a size of the signal region within the image frame, the apparatus may determine whether to change the auto-exposure value threshold.

An illustrative method for managing auto-exposure of image frames may include various operations described herein, each of which may be performed by a computing device such as an auto-exposure management apparatus described herein. For example, the method may include determining a size of a signal region within an image frame captured by an image capture system. The signal region may be identified within the image frame to include pixels having auto-exposure values exceeding an auto-exposure value threshold. The method may further include adjusting, based on the auto-exposure values of the pixels included within the signal region, one or more auto-exposure parameters used by the image capture system to capture an additional image frame. Moreover, the method may include determining, based on the size of the signal region within the image frame, whether to change the auto-exposure value threshold.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Figure 1:
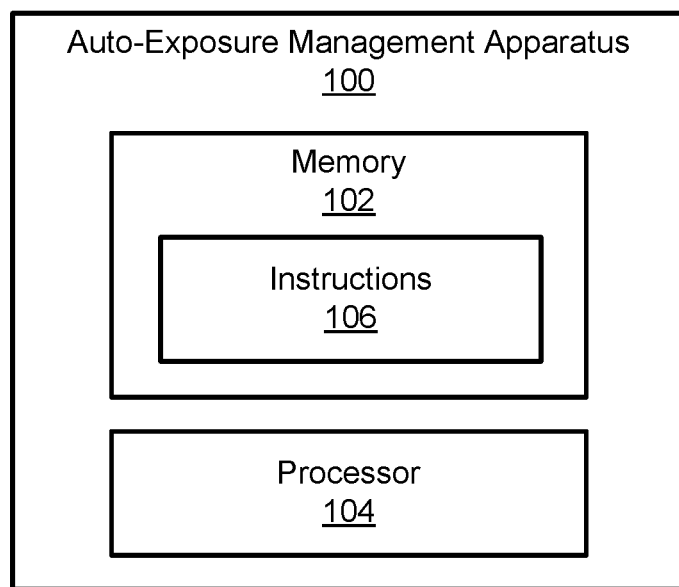
FIG. 1 shows an illustrative auto-exposure management apparatus for managing auto-exposure of image frames according to principles described herein.

Apparatuses, systems, and methods for managing auto-exposure of image frames are described herein. As mentioned above, certain signal content that is displayed against a darkened (e.g., black) background may not be well served by conventional auto-exposure management algorithms. To address this, auto-exposure management that distinguishes and accounts for signal pixels and background pixels may be employed. Even when such auto-exposure management is used, however, certain challenges may arise if the signal pixels are so faint as to be difficult to distinguish from background noise. For example, because the signal content pixels and/or regions may be easily conflated with background noise in such scenarios, many auto-exposure algorithms may treat such signal content the same as the background noise for purposes of auto-exposure management, thereby resulting in image frames that are overexposed or underexposed such that the already faint signal content is even more difficult to see.

As one example of where this type of issue may come into play, an endoscopic image capture device operating in a fluorescence imaging mode will be considered. As described in more detail below, such an image capture device may facilitate a fluorescence-guided medical procedure performed by a user (e.g., a researcher performing an research experiment, a surgeon performing a surgical procedure, staff members assisting with these procedures, etc.) by making it easier for the user to view tissue to which a fluorescence imaging agent has been applied. For example, it may be desirable during certain stages of the medical procedure for staff members to be able to focus exclusively on tissue in which the fluorescence imaging agent has been injected and which therefore fluoresces when illuminated by a fluorescence illumination source. In such instances, imaging instrumentation used for the procedure may generate and provide an image frame sequence that contrasts fluorescence signal content (e.g., the fluorescing tissue to which the fluorescence imaging agent has been applied) against a darkened background so as to facilitate the users in viewing and focusing attention on the signal content.

In certain circumstances (e.g., molecular biomedical research applications, etc.), the fluorescence-guided medical procedures described above may involve fluorescence imaging agents that are extremely diluted (e.g., to a ratio of 1 ppm, etc.). As a result, the fluorescing tissue may be relatively faint or dim and may be difficult to see even when displayed against the darkened background. In some cases, the luminance of the fluorescing tissue may be at a level that is on par with the background noise floor so that pixels included in the signal content are not necessarily any brighter (or much brighter) than noisy pixels included in the background. Consequently, the auto-exposure may overexpose or underexpose images or may generally not behave in a smooth and desirable manner, particularly as various imaging operations (e.g., zooming, panning, etc.) are performed.

Apparatuses, systems, and methods described herein provide auto-exposure management to address these and other issues by, for example, biasing to false positive and treating the brightest content available as being signal content, even if that content is very faint and may include background noise. For example, the brightest one percent (1%), or another suitable percentage depending on the application, of imagery captured may be treated as signal content for purposes of managing auto-exposure, even if there is in fact little or no signal content for a given image frame and this 1% includes or is entirely made up of noise. For viewers of such faint signal content, the tradeoff caused by this false positive bias may be understood and desirable. For example, a researcher or surgeon may prefer to see a bit of extra noise and know that he or she is able to view all of the actual signal content present than to see less noise and risk not seeing some of the actual signal content for certain frames. Additionally, users may benefit from consistent brightness and smooth brightness changes provided by auto-exposure management techniques described herein, particularly when imaging operations such as zooming and panning are performed. Moreover, for image frames that depict signal content that is not particularly faint (e.g., when more than 1% of the image frame is associated with signal content), auto-exposure management described herein may be configured to ignore the effect of the noise and operate based on the detected signal content or operate primarily based on the detected signal content. In this way, both underexposure and overexposure risks may be dynamically mitigated so that an attractive, consistent, and properly-exposed image frame sequence can be generated and presented to the user regardless of how faint or bright the signal content may be at a given moment or for a given procedure.

Fluorescence-guided medical procedure examples such as those introduced above (e.g., fluorescence-guided research experiments, fluorescence-guided surgical procedures, etc.) will be used throughout this description to illustrate various aspects of the claimed subject matter. However, it will be understood that endoscopic images captured using such a fluorescence imaging mode are only intended as examples, and that the principles described herein may be applied, in various implementations, to any suitable types of signal content displayed against any suitable type of background (e.g., a darkened background) as may serve a particular application or use case. As a few additional examples, for instance, auto-exposure management described herein may find application in night vision apparatuses and systems, in low-light camera operating modes, and so forth.

Various specific embodiments will now be described in detail with reference to the figures. It will be understood that the specific embodiments described below are provided as non-limiting examples of how various novel and inventive principles may be applied in various situations. Additionally, it will be understood that other examples not explicitly described herein may also be captured by the scope of the claims set forth below. Apparatuses, systems, and methods described herein may provide any of the benefits mentioned above, as well as various additional and/or alternative benefits that will be described and/or made apparent below.

FIG. 1 shows an illustrative auto-exposure management apparatus 100 (apparatus 100) for managing auto-exposure of image frames according to principles described herein. Apparatus 100 may be implemented by computer resources (e.g., servers, processors, memory devices, storage devices, etc.) included within an image capture system (e.g., an endoscopic image capture device, etc.), by computer resources of a computing system associated with an image capture system (e.g., communicatively coupled to the image capture system), and/or by any other suitable computing resources as may serve a particular implementation.

As shown, apparatus 100 may include, without limitation, a memory 102 and a processor 104 selectively and communicatively coupled to one another. Memory 102 and processor 104 may each include or be implemented by computer hardware that is configured to store and/or process computer software. Various other components of computer hardware and/or software not explicitly shown in FIG. 1 may also be included within apparatus 100. In some examples, memory 102 and processor 104 may be distributed between multiple devices and/or multiple locations as may serve a particular implementation.

Memory 102 may store and/or otherwise maintain executable data used by processor 104 to perform any of the functionality described herein. For example, memory 102 may store instructions 106 that may be executed by processor 104. Memory 102 may be implemented by one or more memory or storage devices, including any memory or storage devices described herein, that are configured to store data in a transitory or non-transitory manner. Instructions 106 may be executed by processor 104 to cause apparatus 100 to perform any of the functionality described herein. Instructions 106 may be implemented by any suitable application, software, code, and/or other executable data instance. Additionally, memory 102 may also maintain any other data accessed, managed, used, and/or transmitted by processor 104 in a particular implementation.

Processor 104 may be implemented by one or more computer processing devices, including general purpose processors (e.g., central processing units (CPUs), graphics processing units (GPUs), microprocessors, etc.), special purpose processors (e.g., application specific integrated circuits (ASICs), field-programmable gate arrays (FPGAs), etc.), image signal processors, or the like. Using processor 104 (e.g., when processor 104 is directed to perform operations represented by instructions 106 stored in memory 102), apparatus 100 may perform various functions associated with managing auto-exposure of image frames depicting signal content against a darkened background. For example, apparatus 100 may perform various functions associated with managing auto exposure of image frames based on signal region size.

Figure 2:
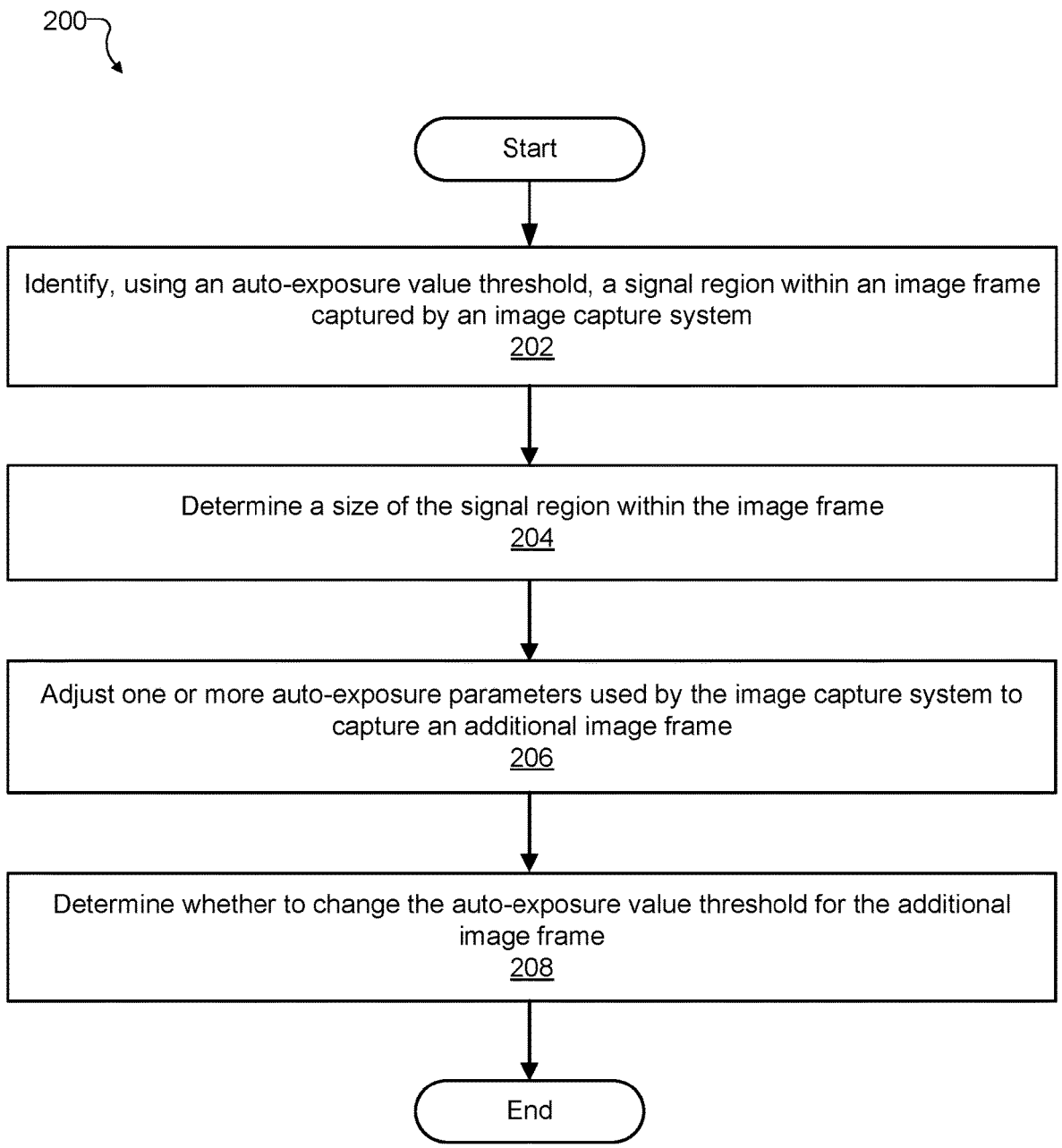
FIG. 2 shows an illustrative auto-exposure management method for managing auto-exposure of image frames according to principles described herein.

FIG. 2 shows an illustrative auto-exposure management method 200 (method 200) that apparatus 100 may perform to manage auto-exposure of image frames in accordance with principles described herein. While FIG. 2 shows illustrative operations according to one embodiment, other embodiments may omit, add to, reorder, and/or modify any of the operations shown in FIG. 2. In some examples, multiple operations shown in FIG. 2 may be performed concurrently (e.g., in parallel) with one another, rather than being performed sequentially as illustrated. One or more of the operations shown in FIG. 2 may be performed by an auto-exposure management apparatus (e.g., apparatus 100), an auto-exposure management system (e.g., an implementation of an auto-exposure management system described below), and/or any implementation thereof.

At operation 202, apparatus 100 may identify, within an image frame captured by an image capture system, a signal region that includes pixels (and/or groups of pixels in certain implementations) that have auto-exposure values exceeding an auto-exposure value threshold. The identified signal region may also exclude pixels (and/or groups of pixels) having auto-exposure values not exceeding the auto-exposure value threshold. Referring to the fluorescence-guided medical procedure examples described above, for instance, the image frame may depict a darkened background over which is displayed tissue that is fluorescing under a fluorescence illumination source due to a presence of a fluorescence imaging agent (e.g., a fluorescence imaging dye, etc.) injected into or otherwise applied to the tissue. In this example, apparatus 100 may identify the signal region to include those parts of the scene that, due to the fluorescing of the tissue, are visible in the image frame and brighter than a brightness associated with the auto-exposure value threshold. In certain examples, apparatus 100 may identify noise or non-signal-related pixels or groups of pixels as part of the signal region if such pixels or pixel groups exceed the auto-exposure value threshold. In this way, the auto-exposure value threshold may be dynamically set and adjusted in a manner that aims to identify at least some portion of the image frame (e.g., 1% of the image frame in certain examples) as being in the signal region even if that portion includes noise and/or other non-signal related pixels.

At operation 204, apparatus 100 may determine a size of the signal region identified at operation 202 within the image frame. The size of the signal region may be determined and represented in any manner as may serve a particular implementation. For example, in certain examples, the size of the signal region may be determined and represented as a percentage such as a percentage representing a portion of the image frame that the signal region covers. As another example, the size of the signal region may be determined and represented as a number of pixels or pixel groups. As yet another example, the size of the signal region may be determined and represented as a ratio, such as a ratio of pixels that exceed the auto-exposure value threshold to pixels that do not exceed the auto-exposure value threshold. In still other examples, the size of the signal region may be determined and represented using other suitable measurements (e.g., area measurements), values, or types of data as may serve to represent the size of the signal region in an absolute sense or with respect to another region (e.g., with respect to the entire image frame, with respect to a background region outside of the identified signal region, etc.).

At operation 206, apparatus 100 may adjust one or more auto-exposure parameters used by the image capture system to capture one or more additional image frames. In some examples, apparatus 100 may adjust the one or more auto-exposure parameters based on auto-exposure values, auto-exposure targets, and/or other auto-exposure data points of the pixels (or pixel groups) identified to be included within the signal region at operation 202. For instance, as part of operation 206, apparatus 100 may determine, based on auto-exposure data points (e.g., auto-exposure values, auto-exposure targets, etc.) of the pixels included within the signal region, an auto-exposure value for the image frame (a frame auto-exposure value) and an auto-exposure target for the image frame (a frame auto-exposure target). Based on the frame auto-exposure value and frame auto-exposure target, system 100 may also determine an auto-exposure gain for the image frame (a frame auto-exposure gain) and may perform the adjusting of the one or more auto-exposure parameters based on the frame auto-exposure gain.

An auto-exposure value will be understood to represent certain auto-exposure-related characteristics (e.g., luminance, signal intensity, chrominance, etc.) of a particular image frame or portion thereof (e.g., region, pixel, group of pixels, etc.). For example, apparatus 100 may detect such characteristics by analyzing the image frame captured by the image capture system. A pixel auto-exposure value may refer to a luminance determined for an individual pixel (e.g., a pixel of the signal region of the image frame as identified at operation 202) or an average luminance determined for a group of pixels in an implementation in which pixels are grouped together into pixel cells in a grid, or the like. As another example, a frame auto-exposure value may refer to an average luminance of some or all of the pixels or pixel groups included within the identified signal region, and, as such, may represent an auto-exposure value that corresponds to the image frame in an analogous way as a pixel auto-exposure value corresponds to a particular pixel or group of pixels.

In these examples, it will be understood that the average luminance (and/or one or more other average exposure-related characteristics in certain examples) referred to by an auto-exposure value may be determined as any type of average as may serve a particular implementation. For instance, an average auto-exposure value for an image frame may refer to a mean luminance of pixels in the signal region of the image frame, determined by summing respective luminance values for each pixel or pixel group of the signal region and then dividing the sum by the total number of values. As another example, an average auto-exposure value for an image frame may refer to a median luminance of pixels in the signal region of the image frame, determined as the central luminance value when all the respective luminance values for each pixel or pixel group of the signal region are ordered by value. As yet another example, an average auto-exposure value for an image frame may refer to a mode luminance of pixels in the signal region of the image frame, determined as whichever luminance value, of all the respective luminance values for each pixel or pixel group of the signal region, is most prevalent or repeated most often. In other examples, other types of averages (besides mean, median, or mode) and other types of exposure-related characteristics (besides luminance) may also be used to determine an auto-exposure value in any manner as may serve a particular implementation.

An auto-exposure target will be understood to refer to a target (e.g., a goal, a desirable value, an ideal, an optimal value, etc.) for the auto-exposure value of a particular image frame or portion thereof (e.g., region, pixel, pixel group, etc.). Apparatus 100 may determine auto-exposure targets based on the particular circumstances and any suitable criteria, and the auto-exposure targets may relate to the same auto-exposure-related characteristics (e.g., luminance, signal intensity, chrominance, etc.) as are represented by the auto-exposure values. For example, auto-exposure targets may be determined at desirable levels of luminance (or other exposure-related characteristics) such as a luminance level associated with middle gray or the like. As such, a pixel auto-exposure target may refer to a desired target luminance determined for an individual pixel (e.g., a pixel of the signal region of the image frame as identified at operation 202) or an average desired target luminance determined for a group of pixels in an implementation in which pixels are grouped together into pixel cells in a grid, or the like. As another example, a frame auto-exposure target may refer to an average desired target luminance for some or all of the pixels or pixel groups included within the identified signal region, and, as such, may represent an auto-exposure target that corresponds to the image frame in an analogous way as a pixel auto-exposure target corresponds to a particular pixel or group of pixels. Similarly as described above in relation to how frame auto-exposure values may be determined, frame auto-exposure targets in such examples may be determined by averaging individual pixel auto-exposure targets using a mean, median, mode, or other suitable type of averaging technique.

Apparatus 100 may perform the adjusting of the one or more auto-exposure parameters at operation 206 based on any or all of the auto-exposure data points (e.g., pixel and/or frame auto-exposure values, pixel and/or frame auto-exposure targets, pixel and/or frame auto-exposure gains, etc.) described herein. For example, once apparatus 100 has determined the auto-exposure data points for the image frame, apparatus 100 may adjust one or more auto-exposure parameters used by the image capture system based on the auto-exposure data points. In this way, the image capture system may capture one or more additional image frames (e.g., subsequent image frames in an image frame sequence being captured) using auto-exposure parameters (e.g., exposure time parameters, shutter aperture parameters, illumination intensity parameters, image signal analog and/or digital gains, etc.) that are likely to reduce the difference between auto-exposure values detected for those additional image frames and auto-exposure targets desirable for those additional image frames. Accordingly, the additional image frames are likely to be captured with more desirable exposure characteristics than might be captured without such adjustments, and users of apparatus 100 are likely to experience a superior image (e.g., an image that shows details at an optimal brightness level, etc.).

At operation 208, apparatus 100 may determine whether to change the auto-exposure value threshold that is used at operation 202 to identify the signal region. For example, apparatus 100 may determine whether to change the auto-exposure value threshold based on the size of the signal region determined at operation 204. By determining whether to change the auto-exposure value threshold based on the size of the signal region, apparatus 100 may control the size of the signal region to ensure that at least a certain portion of the image frame (e.g., 1% in one example) is treated as being part of the signal region regardless of how faint or close to the background noise floor the signal content happens to be. For example, as will be described in more detail below, when the determined size of the signal region dips below a minimum desirable level, apparatus 100 may determine at operation 208 that the auto-exposure value threshold is to change (e.g., decrease) so that the size of the signal region can be increased for subsequent image frames in the image frame sequence. Conversely, when the determined size of the signal region is above the minimum desirable level, apparatus 100 may determine at operation 208 that the auto-exposure value threshold is not to change for subsequent image frames in the image frame sequence.

Apparatus 100 may be implemented by one or more computing devices or by computing resources of a general purpose or special purpose computing system such as will be described in more detail below. In certain embodiments, the one or more computing devices or computing resources implementing apparatus 100 may be communicatively coupled with other components such as an image capture system used to capture the image frames that apparatus 100 is configured to process. In other embodiments, apparatus 100 may be included within (e.g., implemented as a part of) an auto-exposure management system. Such an auto-exposure management system may be configured to perform all the same functions described herein to be performed by apparatus 100 (e.g., including the operations of method 200, described above), but may further incorporate additional components such as the image capture system so as to also be able to perform the functionality associated with these additional components.

Figure 3:
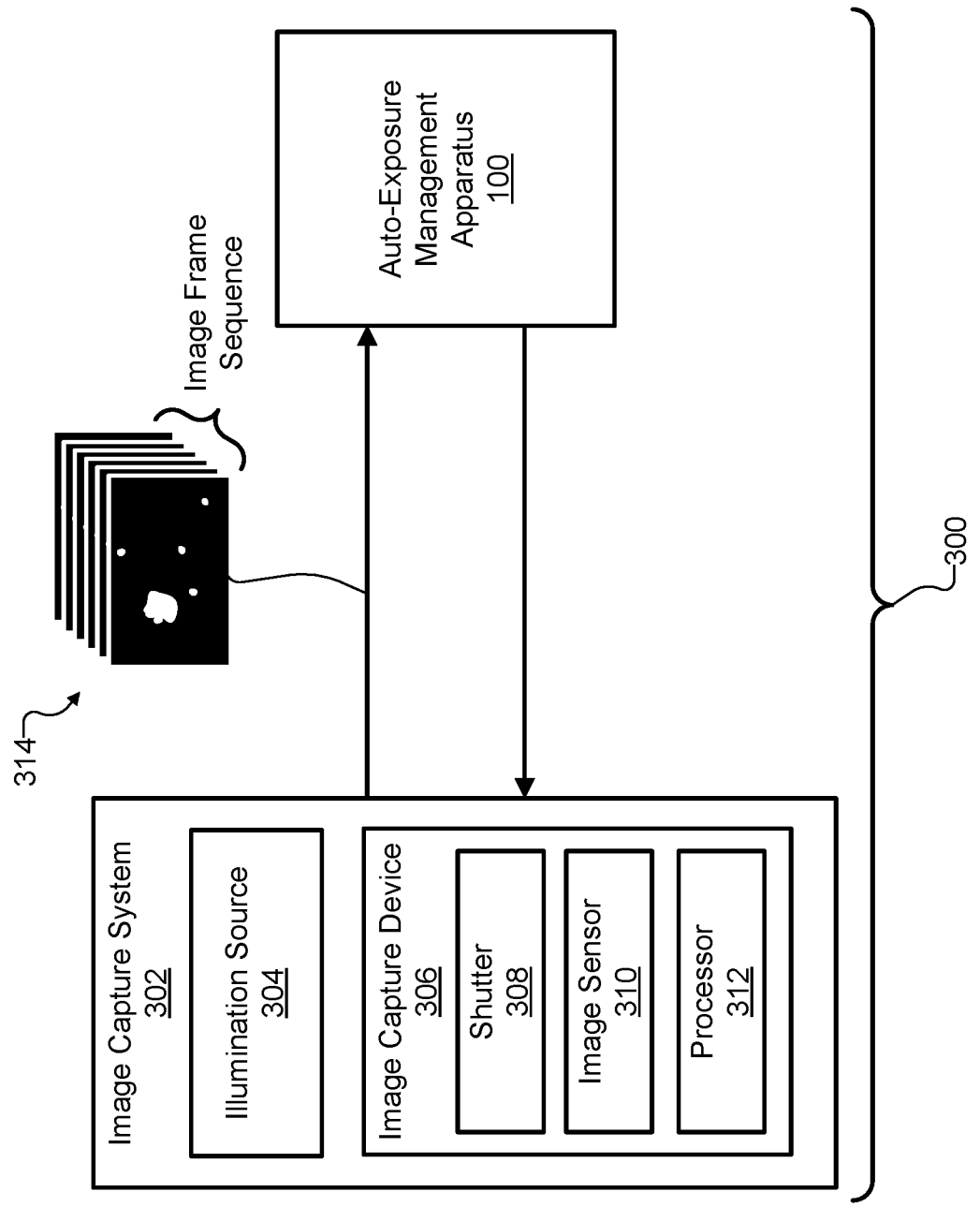
FIG. 3 shows an illustrative auto-exposure management system for managing auto-exposure of image frames according to principles described herein.

FIG. 3 shows an illustrative auto-exposure management system 300 (system 300) for managing auto-exposure of image frames. As shown, system 300 may include an implementation of apparatus 100 together with an image capture system 302 that includes an illumination source 304 and an image capture device 306 that incorporates a shutter 308, an image sensor 310, and a processor 312 (e.g., one or more image signal processors implementing an image signal processing pipeline). Within system 300, apparatus 100 and image capture system 302 may be communicatively coupled to allow apparatus 100 to direct image capture system 302 in accordance with operations described herein, as well as to allow image capture system 302 to capture and provide to apparatus 100 an image frame sequence 314 and/or other suitable captured image data. Components of image capture system 302 will now be described.

Illumination source 304 may be implemented by any type of source of illumination (e.g., visible light, fluorescence excitation light such as near infrared light, etc.) and may be configured to interoperate with image capture device 306 within image capture system 302. For example, illumination source 304 may provide a certain amount of illumination to a scene to facilitate image capture device 306 in capturing optimally illuminated images of the scene. As has been mentioned, while principles described herein may be applied to a wide variety of imaging scenarios, many examples explicitly described herein relate to medical procedures (e.g., fluorescence-guided medical procedures) performed using a computer-assisted medical system such as will be described in more detail below in relation to FIG. 10. In such examples, the scene for which images are being captured may include an operational area associated with a body on which the medical procedure is being performed (e.g., a body of a live animal, a human or animal cadaver, a portion of human or animal anatomy, tissue removed from human or animal anatomies, non-tissue work pieces, training models, etc.), and system 300 or certain components thereof (e.g., image capture system 302) may be integrated with (e.g., implemented by imaging and computing resources of) a computer-assisted medical system. In examples involving a fluorescence-guided medical procedure, illumination source 304 may include a fluorescence illumination (e.g., excitation) source configured to illuminate tissue within the body undergoing the fluorescence-guided medical procedure. A portion of the tissue may include (e.g., may be injected with) a fluorescence imaging agent that fluoresces when illuminated by the fluorescence illumination source.

Image capture device 306 may be implemented by any suitable camera or other device configured to capture images of a scene. For instance, in a medical procedure example, image capture device 306 may be implemented by an endoscopic image capture device configured to capture image frame sequence 314, which may include an image frame depicting a view (e.g., an internal view) of the body undergoing the fluorescence-guided medical procedure. In some examples, the image frame may depict fluorescence content against a darkened background, where the fluorescence content is generated by a fluorescence imaging agent that fluoresces when illuminated by a fluorescence illumination source (e.g., a source implemented by or included within illumination source 304). The fluorescence imaging agent may be diluted to a great degree in some situations. For instance, the fluorescence imaging agent may be diluted to a degree that at least a portion of the fluorescence content is associated with an auto-exposure value less than an auto-exposure value associated with at least a portion of noise within the image frame. Accordingly, the signal region of the image frame that will be identified by apparatus 100 (e.g., when performing operation 202 of method 200 on the image frame) may correspond to the fluorescence content and/or to the noise within the image frame based on whether the auto-exposure values associated with the fluorescence content and the noise exceed the auto-exposure value threshold. As shown, image capture device 306 may include components such as shutter 308, image sensor 310, and processor 312.

Image sensor 310 may be implemented by any suitable image sensor, such as a charge coupled device (CCD) image sensor, a complementary metal-oxide semiconductor (CMOS) image sensor, or the like.

Shutter 308 may interoperate with image sensor 310 to assist with the capture and detection of light from the scene. For example, shutter 308 may be configured to expose image sensor 310 to a certain amount of light for each image frame captured. Shutter 308 may comprise an electronic shutter and/or a mechanical shutter. Shutter 308 may control how much light image sensor 310 is exposed to by opening to a certain aperture size defined by a shutter aperture parameter and/or for a specified amount of time defined by an exposure time parameter. As will be described in more detail below, these shutter-related parameters may be included among the auto-exposure parameters that apparatus 100 is configured to adjust.

Processor 312 may be implemented by one or more image signal processors configured to implement at least part of an image signal processing pipeline. Processor 312 may process auto-exposure statistics input (e.g., by tapping the signal in the middle of the pipeline to detect and process various auto-exposure data points and/or other statistics), perform optics artifact correction for data captured by image sensor 310 (e.g., by reducing fixed pattern noise, correcting defective pixels, correcting lens shading issues, etc.), perform signal reconstruction operations (e.g., white balance operations, demosaic and color correction operations, etc.), apply image signal analog and/or digital gains, and/or perform any other functions as may serve a particular implementation. Various auto-exposure parameters may dictate how the functionality of processor 312 is to be performed. For example, auto-exposure parameters may be set to define the analog and/or digital gains processor 312 applies, as will be described in more detail below.

In some examples, an endoscopic implementation of image capture device 306 may include a stereoscopic endoscope that includes two full sets of image capture components (e.g., two shutters 308, two image sensors 310, etc.) to accommodate stereoscopic differences presented to the two eyes (e.g., left eye and right eye) of a viewer of the captured image frames. Conversely, in other examples, an endoscopic implementation of image capture device 306 may include a monoscopic endoscope with a single shutter 308, a single image sensor 310, and so forth.

Apparatus 100 may be configured to control various auto-exposure parameters of image capture system 302 and may adjust such auto-exposure parameters in real time based on incoming image data captured by image capture system 302. As mentioned above, certain auto-exposure parameters of image capture system 302 may be associated with shutter 308 and/or image sensor 310. For example, apparatus 100 may direct shutter 308 in accordance with an exposure time parameter corresponding to how long the shutter is to allow image sensor 310 to be exposed to the scene, a shutter aperture parameter corresponding to an aperture size of shutter 308, or any other suitable auto-exposure parameters associated with shutter 308. Other auto-exposure parameters may be associated with aspects of image capture system 302 or the image capture process unrelated to shutter 308 and/or sensor 310. For example, apparatus 100 may adjust an illumination intensity parameter of illumination source 304 that corresponds to an intensity of illumination provided by illumination source 304, an illumination duration parameter corresponding to a time period during which illumination is provided by illumination source 304, or the like. As yet another example, apparatus 100 may adjust gain parameters corresponding to one or more analog and/or digital gains (e.g., analog gains, bayer gains, RGB gains, etc.) applied by processor 312 to luminance data generated by image sensor 310.

Any of these or other suitable parameters, or any combination thereof, may be updated and/or otherwise adjusted by apparatus 100 for subsequent image frames based on an analysis of the current image frame. For instance, in one example where the frame auto-exposure gain (e.g., the frame auto-exposure target divided by the frame auto-exposure value) is determined to be 6.0, various auto-exposure parameters could be set as follows: 1) a current illumination intensity parameter may be set to 100% (e.g., maximum output); 2) an exposure time parameter may be set to $\frac{1}{60}^{th}$ of a second (e.g., 60 fps); 3) an analog gain may be set to 5.0 (with a cap of 10.0); 4) a bayer gain may be set to 1.0 (with a cap of 3.0); and 5) an RGB gain may be set to 2.0 (with a cap of 2.0). With these settings, the gain is distributed across the analog gain (10.0/5.0=2.0), bayer gain (3.0/1.0=3.0), and RGB gain (2.0/2.0=1.0) to establish the desired 6.0 total auto-exposure gain (3.0*2.0*1.0=6.0) for the frame.

In certain examples, image capture system 302 may employ a fluorescence imaging mode to generate image frame sequence 314 in a manner that emphasizes signal content associated with fluorescing tissue by displaying the fluorescence signal content against a darkened background such as a black background.

Figure 4:
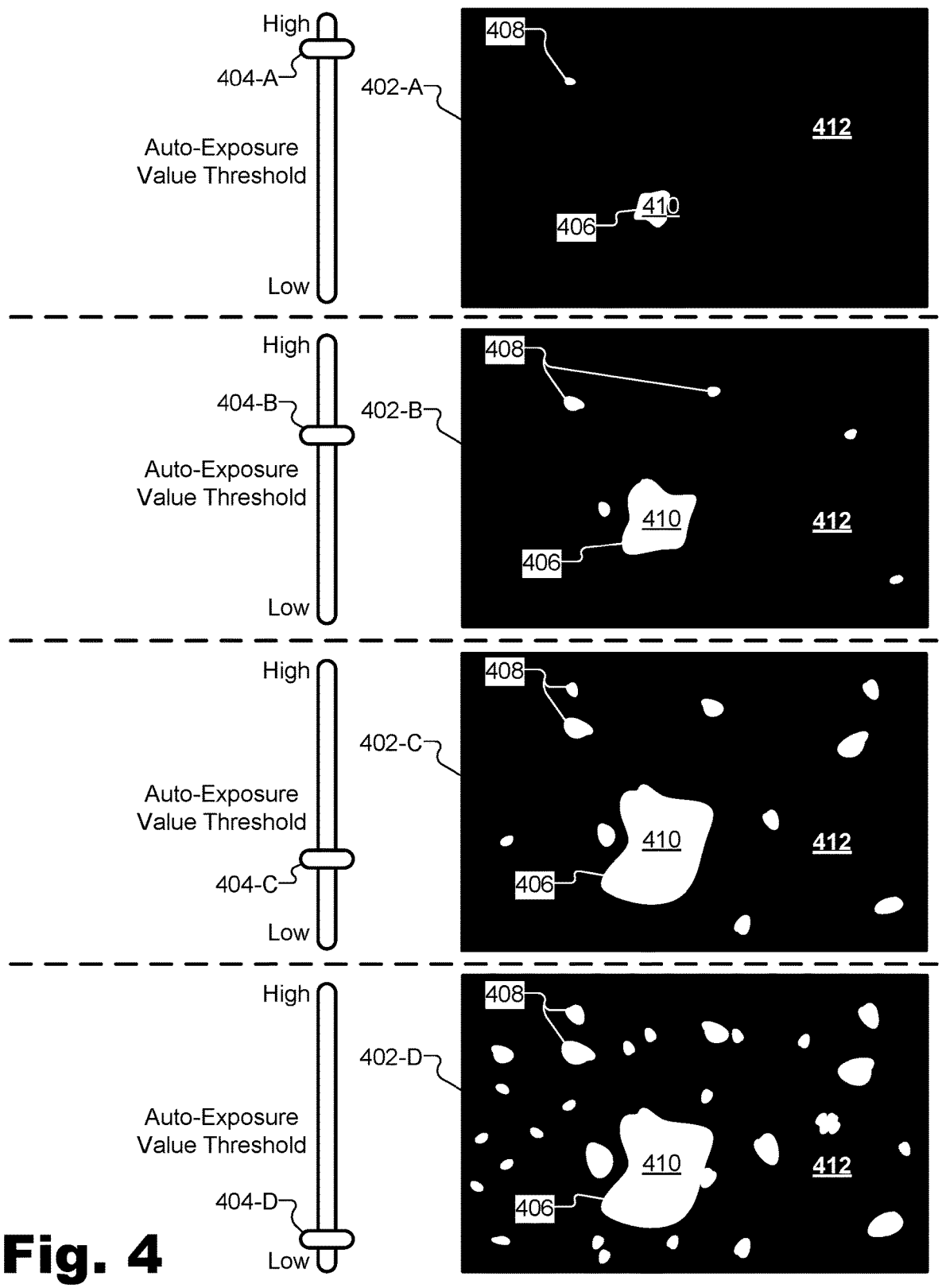
FIG. 4 shows illustrative image frames according to principles described herein.

FIG. 4 shows illustrative image frames 402 (e.g., image frames 402-A through 402-D) that depict signal content against a darkened background and that represent examples of individual image frames from an image frame sequence such as image frame sequence 314 of FIG. 3. As shown in FIG. 4, each image frame 402 is associated with a different auto-exposure value threshold 404 (e.g., a high auto-exposure value threshold 404-A for image frame 402-A, a medium-high auto-exposure value threshold 404-B for image frame 402-B, a medium-low auto-exposure value threshold 404-C for image frame 402-C, and a low auto-exposure value threshold 404-D for image frame 402-D). Within each image frame 402, signal content 406 and noise 408 are shown against a darkened background (e.g., the blackness upon which the white signal content 406 and noise 408 is shown). All of the white content shown in image frames 402 (e.g., signal content 406 and noise 408, collectively) may be collectively identified as signal region 410 in each image frame 402, while all of the darkened background other than signal content 406 and noise 408 may be excluded from signal region 410 and collectively identified as a background region 412.

In some examples, image frames such as image frames 402 may depict, against the darkened background, fluorescence content that is generated by a fluorescence imaging agent (e.g., indocyanine green (ICG), etc.) injected into tissue so as to make the tissue fluoresce when illuminated (e.g., excited) by a fluorescence illumination source. For example, an image capture system that includes an endoscopic image capture device may capture image frames like image frames 402 while operating in a fluorescence imaging mode as part of a fluorescence-guided medical procedure. In the fluorescence image mode, fluorescing tissue may be visible while other areas that are not emitting fluorescence light (e.g., other anatomy surrounding the injected tissue, instrumentation and/or other objects, etc.) may remain dark. In examples where image frames 402 depict this type of imagery, signal region 410 may correspond to the fluorescence content (e.g., the injected tissue fluorescing due to the presence of the fluorescing imaging agent), and background region 412 may correspond to the darkened background (e.g., portions of the body and/or other objects and instrumentation at the scene not having the fluorescence imaging agent). In other examples, image frames 402 may represent other types of signal content against other types of darkened backgrounds (e.g., signal content and backgrounds unrelated to fluorescence imaging or medical procedures), or any other type of image as may be served by apparatuses, systems, and/or methods described herein.

As shown progressively by the sequence of image frames 402-A to 402-D, a size of signal region 410 may change as the level of the auto-exposure value threshold 404 changes. Specifically, as shown, as auto-exposure value threshold 404 changes from being a relatively high threshold (at auto-exposure value threshold 404-A) to being a relatively low threshold (at auto-exposure value threshold 404-D), signal region 410 changes from having a relatively small size (at image frame 402-A) to having a relatively large size (at image frame 402-D). This is because as auto-exposure value threshold 404 decreases, the pixel auto-exposure values of more and more pixels (e.g., including pixels of both signal content 406 and noise 408) come to exceed the auto-exposure value threshold and are hence identified as being part of signal region 410. Conversely, as auto-exposure value threshold 404 increases, the pixel auto-exposure values of fewer and fewer pixels (e.g., including pixels of noise 408 and potentially pixels of signal content 406) are able to exceed the auto-exposure value threshold and are hence not identified as being part of signal region 410.

FIG. 4 illustrates how the size of signal region 410 may be controlled by adjusting auto-exposure value threshold 404. For example, if the size of signal region 410 is relatively small (e.g., as in image frame 402-A), the size of signal region 410 may be increased for subsequent frames by gradually lowering auto-exposure value threshold 404 until the size of signal region 410 achieves a suitable level. As another example, if it is determined that signal region 410 includes all of signal content 406 but also includes more noise 408 than necessary (e.g., as may be the case in image frame 402-D, where the same signal content 406 is shown as included in image frame 402-C but significantly more noise 408 is shown than is included in image frame 402-C), the size of signal region 410 may be decreased and noise omitted for subsequent frames by gradually raising auto-exposure value threshold 404 (e.g., until a certain baseline threshold is reached). Various benefits of controlling the size of a signal region used for managing auto-exposure of image frames are described herein, particularly in relation to examples where the signal content of an image frame is faint (e.g., having a luminance on par with the background noise) and it is desirable for the signal region to be identified using a bias toward false positive.

Figure 5:
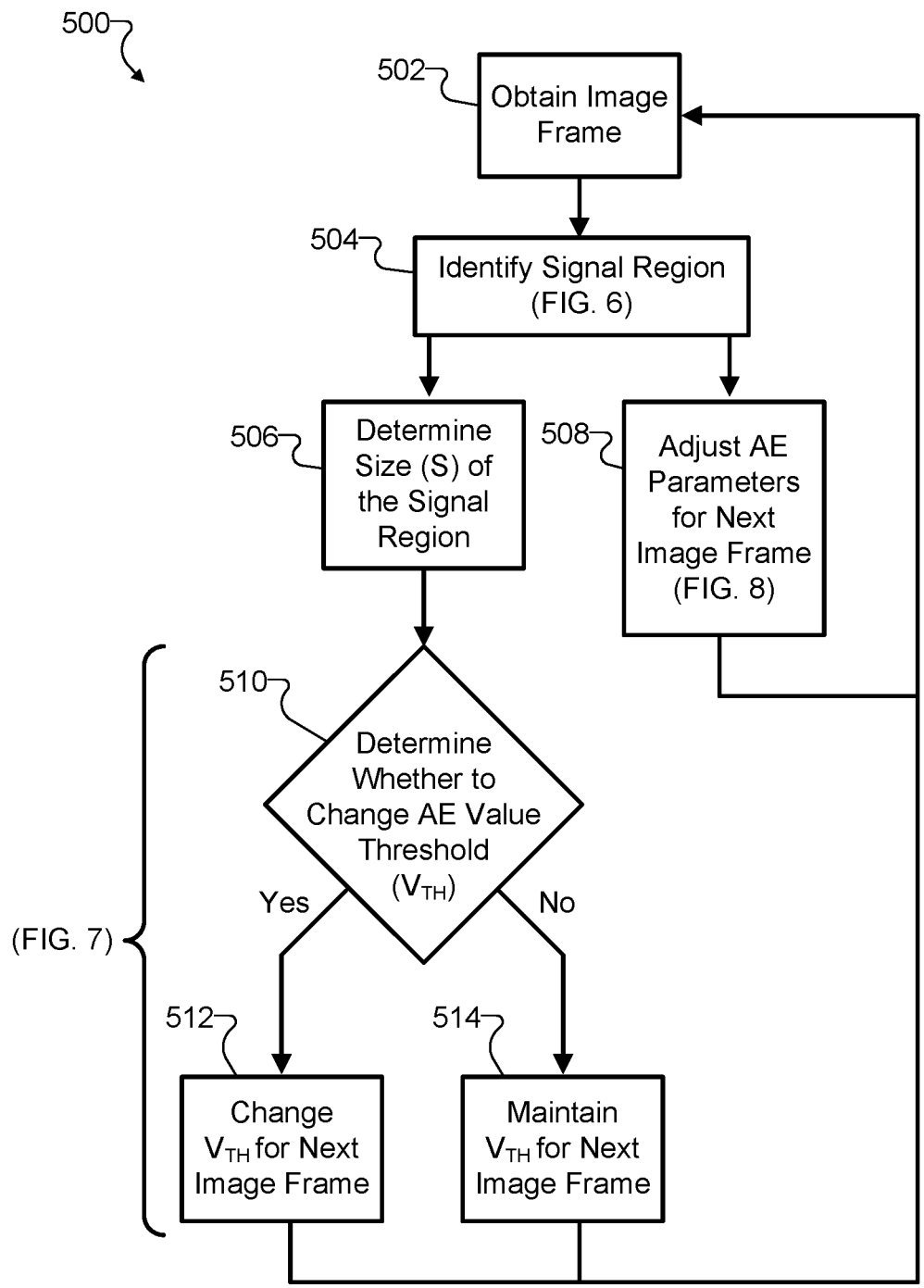
FIG. 5 shows an illustrative flow diagram for managing auto-exposure of image frames according to principles described herein.

FIG. 5 shows an illustrative flow diagram 500 for managing auto-exposure of image frames using, for example, an implementation of apparatus 100, method 200, and/or system 300. As shown, flow diagram 500 illustrates various operations 502-514, which will each be described in more detail below. It will be understood that operations 502-514 represent one embodiment, and that other embodiments may omit, add to, reorder, and/or modify any of these operations. As will be described, various operations 502-514 of flow diagram 500 may be performed for one image frame or multiple image frames (e.g., each image frame) in an image frame sequence. It will be understood that, depending on various conditions, not every operation might be performed for every frame, and the combination and/or order of operations performed from frame to frame in the image frame sequence may vary.

At operation 502, an image frame (e.g., a fluorescence image frame, a visible light image frame, a combination thereof, etc.) that has been captured by an image capture system may be obtained (e.g., accessed, loaded, captured, generated, etc.). As previously explained, in certain examples, the image frame may be an image frame depicting signal content against a darkened background (e.g., such as one of image frames 402 described above). Operation 502 may be performed in any suitable way, such as by accessing the image frame from an image capture system (e.g., in the case that operation 502 is being performed by an implementation of apparatus 100 that is communicatively coupled to an image capture system) or by using an integrated image capture system to capture the image frame (e.g., in the case that operation 502 is being performed by an implementation of system 300 that includes integrated image capture system 302).

At operation 504, apparatus 100 may identify a signal region in the obtained image frame based on an auto-exposure value threshold. For example, as illustrated in FIG. 4, if the image frame obtained at operation 502 is one of image frames 402-A through 402-D, apparatus 100 may identify the respective signal regions 410 of these image frames based on the different respective levels at which auto-exposure value threshold 404 is set. In this way, a relatively large signal region may be identified, for example, when the auto-exposure value threshold is relatively low, while a relatively small signal region may be identified when the auto-exposure value threshold is relatively high.

In some examples, identifying the signal region may include distinguishing the signal region (e.g., signal region 410) from a background region (e.g., background region 412) by determining, for each pixel or pixel group within the image frame, whether the pixel auto-exposure value exceeds or fails to exceed the current auto-exposure value threshold. Pixels having auto-exposure values exceeding the auto-exposure value threshold may be identified to be included within the signal region while pixels having auto-exposure values that do not exceed the auto-exposure value threshold may be identified to be excluded from the signal region (e.g., to be included within the background region).

Figure 6:
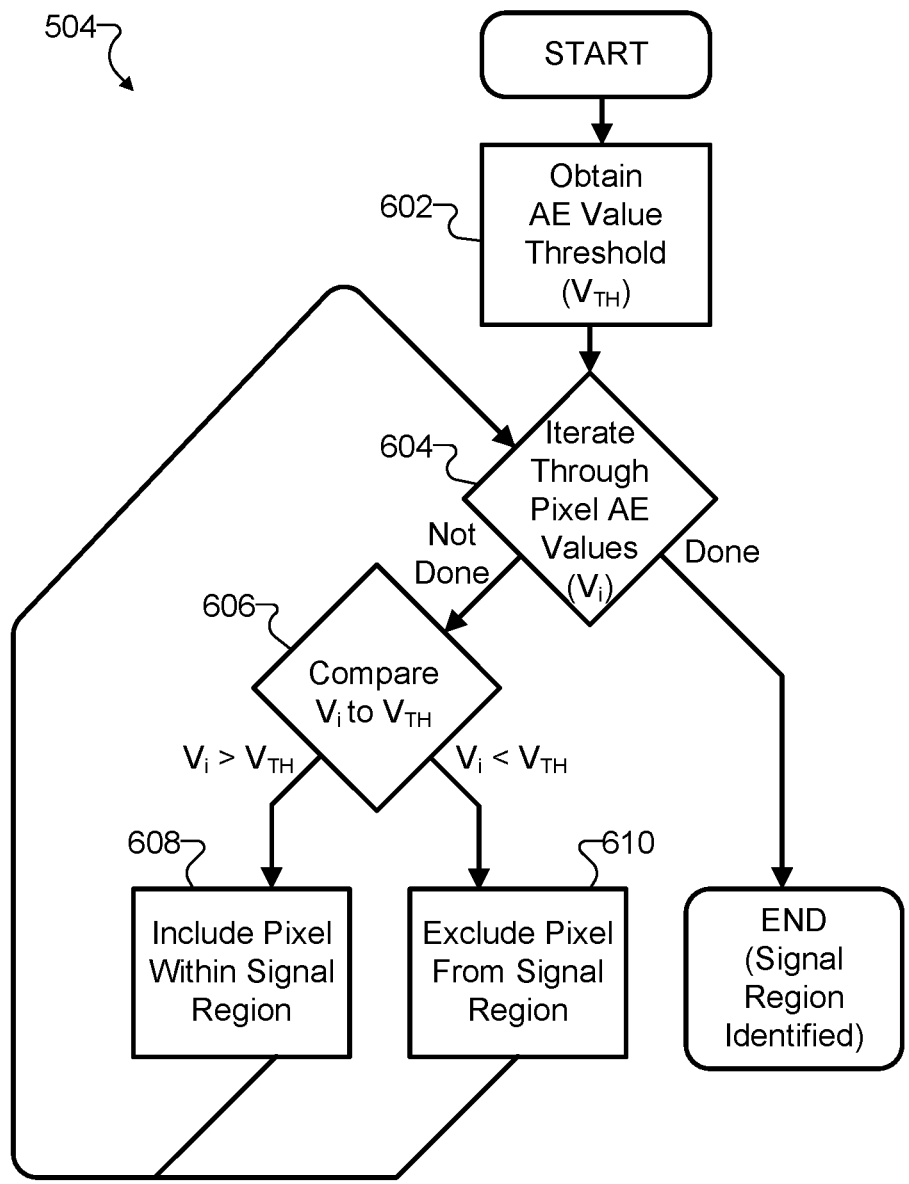
FIG. 6 shows an illustrative flow diagram for identifying a signal region within an image frame according to principles described herein.

To illustrate, FIG. 6 shows an illustrative flow diagram for identifying a signal region within an image frame at operation 504. The flow diagram of operation 504 is shown in FIG. 6 to include a plurality of operations 602-610 that may be performed between when operation 504 begins (labeled START) and when operation 504 is complete and the signal region is identified (labeled END).

At operation 602, apparatus 100 may determine an auto-exposure value threshold ($V_{TH}$). The auto-exposure value threshold may be determined in any suitable way. For example, as will be described in more detail below, the auto-exposure value threshold may be a frame-specific dynamic threshold that may be initially set based on a baseline auto-exposure value threshold (described in more detail below), and that may be continuously monitored and potentially updated to control the size of the signal region (e.g., to maintain the size of the signal region greater than a predetermined minimum threshold size). Accordingly, obtaining the auto-exposure value threshold at operation 602 may include accessing the current value for the auto-exposure value threshold or updating a previous value of the auto-exposure value threshold in any of the ways that will be described below in relation to FIG. 7. In some examples, the updating of the auto-exposure value threshold may include scaling the auto-exposure value threshold by one or more gains (e.g., the analog gain determined for the current frame, the bayer gain that has been determined for the current frame, etc.) at operation 602 prior to using the auto-exposure value threshold for comparison purposes at operation 606, described below.

At operation 604, apparatus 100 may iterate through each pixel of an image frame or portion of an image frame (or each cell or group of pixels in implementations that may operate on such groupings rather than on individual pixels). For each pixel i, an auto-exposure value of the pixel ($V_i$) may be compared to the auto-exposure value threshold ($V_{TH}$) at operation 606. As mentioned above, the auto-exposure value threshold may be scaled by one or more gains for the frame (e.g., the analog gain, the bayer gain, etc.) before being used at operation 606 for making comparisons that allow apparatus 100 to sort which pixels are to be included within the signal region. As shown, the comparisons and sorting of pixels may continue for as long as there are still pixels (or pixel groups) of the image frame that have not yet been analyzed (Not Done), and may end when all of the pixels of the image frame have been iterated through (Done). In certain examples, rather than iterating through all of the pixels of the image frame, a certain region of the image frame (e.g., a central region of the image frame such as a central 50% of the image frame, a central 80% of the image frame, etc.) may be accounted for while another region of the image frame (e.g., a peripheral region of the image frame such as an outer 50% of the image frame, an outer 20% of the image frame, etc.) may be ignored for purposes of auto-exposure management. In such examples, operation 504 may finish iterating (Done) when all the pixels of the region that is to be accounted for (e.g., the central region) have been iterated through. At operation 606, the comparison between the pixel auto-exposure value and the auto-exposure value threshold may be configured to provide one of two outcomes: (1) the pixel auto-exposure value may exceed the auto-exposure value threshold ($V_i > V_{TH}$); or (2) the pixel auto-exposure value might not exceed the auto-exposure value threshold ($V_i < V_{TH}$). It will be understood that, in the event that the pixel auto-exposure value is equal to the auto-exposure value threshold, the pixel auto-exposure value may be counted as exceeding or not exceeding the auto-exposure value threshold as may serve a particular implementation.

Pixels having auto-exposure values that exceed the auto-exposure value threshold may be identified to be included in the signal region at operation 608. Conversely, pixels having auto-exposure values that do not exceed the auto-exposure value threshold may be identified to be excluded from the signal region (e.g., and included in the background region) at operation 610. Flow may then proceed from operation 608 or 610 back to operation 604 where the next pixel or group of pixels may be analyzed until the image frame (e.g., the entire image frame or a portion of the image frame) has been processed and the signal has been successfully identified.

While FIG. 6 shows one suitable way for identifying the signal region of an image frame, it will be understood that other ways of achieving the same or a similar outcome may also be employed in other implementations. For example, certain implementations may involve determining probabilities for each pixel (or pixel grouping) and identifying the pixels in the signal region based on their respective probabilities, or performing similar auto-exposure value threshold or probability comparisons on groupings of pixels (e.g., cells of a grid into which the pixels could be subdivided) rather than individual pixels.

Returning to FIG. 5, after the signal region is identified at operation 504, flow may proceed to either or both of operations 506 and 508. Because operations 506 and 508 are not necessarily dependent on one another, these operations may be performed for the current image frame independently and in any order or in parallel with one another.

At operation 506, apparatus 100 may determine a size (S) of the signal region identified at operation 504. This size may be referred to as a signal region size value, and, as will be described in more detail below, may be used to determine whether to change the auto-exposure value threshold for subsequent image frames. The signal region size value may be determined so as to represent the size of the identified signal region of the image frame in any of the ways described herein. For example, as mentioned above, the signal region size value may represent the size of the signal region by being set to an area of the signal region, a total number of pixels (or pixel groupings or cells) included in the signal region, a total percentage of pixels included in the signal region compared to the total number of pixels included in the image frame, a ratio of pixels included in the signal region to pixels excluded from the signal region, or any other value that represents the size, significance, prominence, or other such characteristic of the signal region as may serve a particular implementation.

At operation 510, the signal region size value may be used to determine whether to change the auto-exposure value threshold. In some examples, the determining whether to change the auto-exposure value threshold at operation 510 by apparatus 100 may include determining to change the auto-exposure value threshold (Yes). For example, apparatus 100 may determine to change the auto-exposure value threshold to a value targeted to maintain the size of the signal region at or above a signal region size threshold. In response, flow may proceed to operation 512, where apparatus 100 may control the size of the signal region by changing (e.g., dynamically changing), based on the determining to change the auto-exposure value threshold, the auto-exposure value threshold to the value targeted to maintain the size of the signal region at or above the signal region size threshold. As such, when an additional frame (e.g., the subsequent frame) is later obtained, apparatus 100 may use the changed auto-exposure value threshold (e.g., the value targeted to maintain the size of the signal region at or above the signal region size threshold) to perform the operations of flow diagram 500 for the additional frame. For example, apparatus 100 may identify, within the additional frame, a second signal region that includes pixels having auto-exposure values exceeding the changed auto-exposure value threshold (operation 504), and may adjust, based on the auto-exposure values of the pixels included within the second signal region, the one or more auto-exposure parameters used by the image capture system to capture yet another image frame (operation 508).

In other examples, the determining whether to change the auto-exposure value threshold at operation 510 by apparatus 100 may include determining not to change the auto-exposure value threshold (No). In response, flow may proceed to operation 514, where apparatus 100 may control the size of the signal region by maintaining the auto-exposure value threshold at a baseline auto-exposure value threshold based on the determining not to change the auto-exposure value threshold.

In either situation, apparatus 100 may control the size of the signal region in a manner targeted at maintaining the size of the signal region at or above a signal region size threshold (e.g., at least 1% of the image frame in one example, 2% in another example, 5% in another example, etc.) for subsequent image frames (e.g., the next image frame) in the image frame sequence for which apparatus 100 is managing the auto-exposure. For example, control exerted by apparatus 100 may attempt to increase the signal region size value to at least the level of the signal region size threshold whenever the signal region size value dips below the signal region size threshold by gradually decreasing the auto-exposure value threshold. Additionally, once the signal region size value returns to at least the desired signal region size threshold, the control exerted by apparatus 100 may gradually increase the auto-exposure value threshold again until reaching a baseline (e.g., maximum) auto-exposure value threshold. In this way, the control performed by apparatus 100 may ensure that changes to the auto-exposure value threshold occur gradually and smoothly to avoid undesirable auto-exposure artifacts that could occur if the auto-exposure value threshold were to be changed too abruptly.

Figure 7:
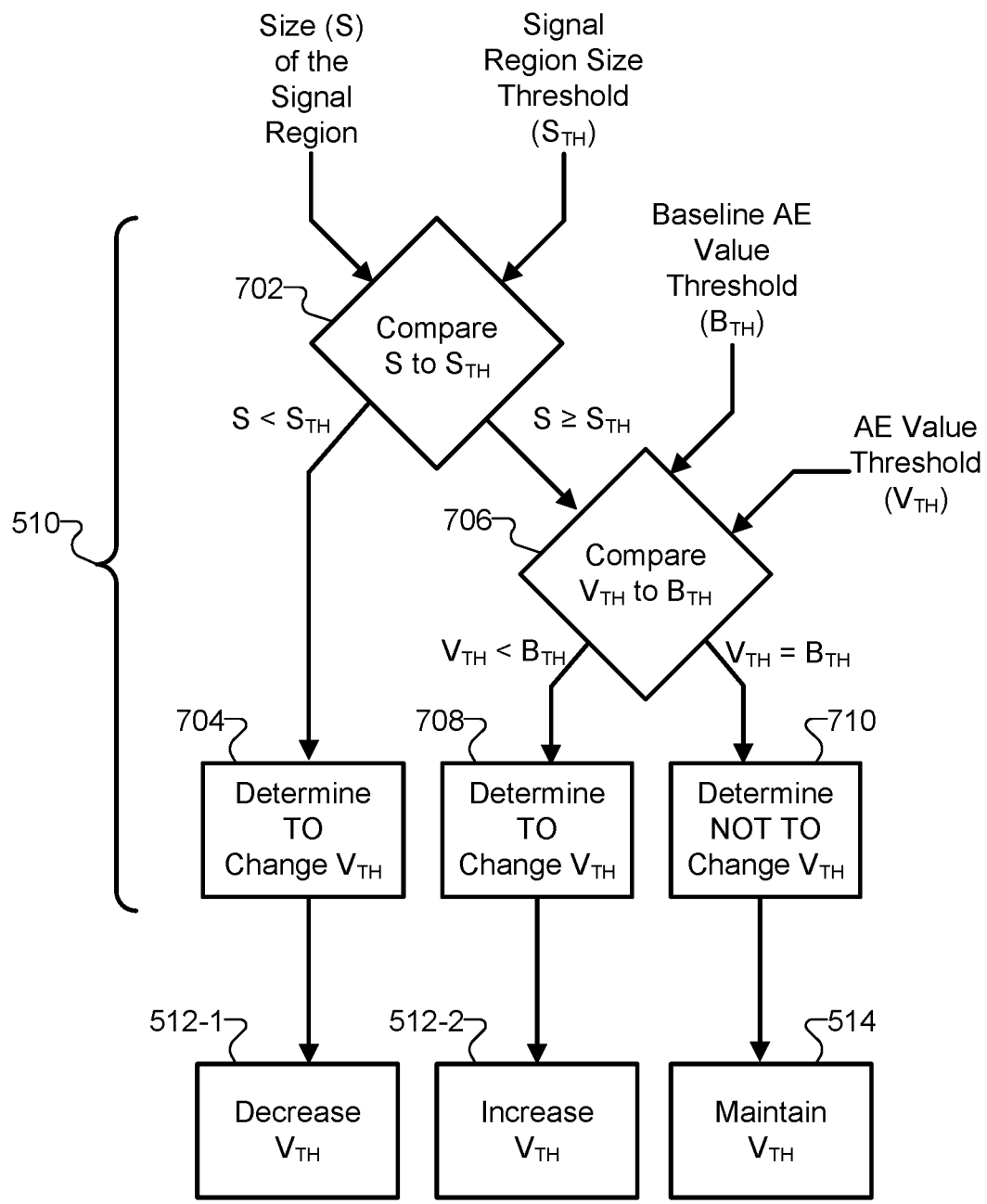
FIG. 7 shows an illustrative flow diagram for controlling a size of a signal region within an image frame sequence by dynamically changing an auto-exposure value threshold according to principles described herein.

FIG. 7 shows an illustrative flow diagram for controlling a size of a signal region within an image frame sequence by dynamically changing an auto-exposure value threshold according to principles described herein. As such, and as indicated in FIG. 5, FIG. 7 may be understood to represent a more detailed flow diagram of operations 510, 512, and 514. Specifically, as shown, operation 510 of FIG. 5 may correspond to one or more of operations 702-710 (performed in accordance with the flow illustrated in FIG. 7), operation 512 of FIG. 5 may correspond to operations 512-1 and 512-2 of FIG. 7, and operation 514 of FIG. 5 may correspond to operation 514 of FIG. 7.

At operation 702, apparatus 100 may compare the size (S) of the signal region (the signal region size value) to a minimum desirable threshold ($S_{TH}$) for the size of the signal region (the signal region size threshold). For example, a signal region size threshold could be a total of 1% of the image frame, another suitable proportion of the image frame (e.g., 2%, 10%, etc.), or another size threshold represented as a ratio, a number of pixels or pixel groups, or the like.

In some scenarios, a determination may be made that the size of the signal region is less than the signal region size threshold. Based on that determination, apparatus 100 may determine that the auto-exposure value threshold is to be changed (e.g., decreased). As one example, FIG. 7 shows that the comparison at operation 702 may reveal that the signal region size value is less than the signal region size threshold ($S<S_{TH}$), thereby leading the control algorithm to operation 704, where apparatus 100 determines that the auto-exposure value threshold is to be changed (e.g., determining to decrease the auto-exposure value threshold). In this example, the size of the signal region may be smaller than is desired, and the control algorithm may thus be configured to attempt to increase the size of the signal region by decreasing the auto-exposure value threshold. For instance, signal content in the image frame may be so faint as to be on par with some background noise, and there may therefore be a risk that signal content could be conflated with background noise and hence not be properly accounted for in the auto-exposure management. Accordingly, flow is shown to proceed to operation 512-1, where apparatus 100 may decrease (e.g., dynamically decrease or decrement) the auto-exposure value threshold based on the determining to decrease the auto-exposure value threshold at operation 704. As such, when an additional frame (e.g., the subsequent frame) is later obtained, apparatus 100 may use the decreased auto-exposure value threshold to perform the operations of flow diagram 500 for the additional frame. For example, apparatus 100 may identify, within the additional frame, a second signal region that includes pixels having auto-exposure values exceeding the decreased auto-exposure value threshold (operation 504), and may determine, based on a size of the second signal region (operation 506), whether to further change the decreased auto-exposure value threshold such as by further decreasing the auto-exposure value threshold or increasing the auto-exposure value threshold (operation 510).

In some implementations, decreasing the auto-exposure value threshold at operation 512-1 may be performed in a stepwise manner by decrementing the auto-exposure value threshold by a particular incremental value (e.g., a relatively small, static value), rather than by a dynamic value that is determined proportionally to, for instance, how far the signal region size value is detected to be below the signal region size threshold. In this way, it may take a few frames and a little time for the auto-exposure management to fully account for the drop of the signal region size value below the signal region size threshold, especially in cases where the drop is relatively sudden and the difference between the value and the threshold is significant. On the other hand, an advantage of making stepwise changes in this way is that the resultant auto-exposure management may be smooth and consistent rather than varying widely in a potentially distracting manner.

In other implementations, decreasing the auto-exposure value threshold at operation 512-1 may be performed in a more instantaneous manner. For example, apparatus 100 may determine how much to decrease the auto-exposure value threshold based on the difference between the signal region size value and the signal region size threshold or other suitable factors, and may decrease the auto-exposure value threshold all at once to attempt to more quickly increase the signal region size value to reach or exceed the signal region size threshold. In contrast to the stepwise technique described above, this instantaneous technique may be more responsive to stark and sudden changes in signal region size, but may also result in auto-exposure management that appears less smooth and/or consistent. In some examples, a combination of the stepwise and instantaneous techniques may be employed to achieve some of the advantages, or to mitigate some of the potential drawbacks, of each of the techniques.

Returning to operation 702, in some scenarios, a determination may be made that the size of the signal region is at or above the signal region size threshold. As one example, FIG. 7 shows that the comparison at operation 702 may reveal that the signal region size value is greater than or equal to the signal region size threshold ($S \geq S_{TH}$), thereby leading the control algorithm to operation 706, where apparatus 100 accounts for other considerations to determine whether to change (e.g., increase) the auto-exposure value threshold. Specifically, as shown at operation 706, apparatus 100 may compare the current auto-exposure value threshold ($V_{TH}$) to a baseline auto-exposure value threshold ($B_{TH}$) that may be representative of a maximum desirable auto-exposure value threshold. Based on this comparison, a determination is made at operation 706 regarding whether the auto-exposure value threshold is at (or above) the baseline auto-exposure value threshold ($V_{TH} \geq B_{TH}$), or whether the auto-exposure value threshold is below the baseline auto-exposure value threshold ($V_{TH} < B_{TH}$). For example, if a relatively large amount of relatively strong and stable signal content has been present for several image frames, the determination made at operation 706 is likely to be that the auto-exposure value threshold is stable at the baseline auto-exposure value threshold and does not need to be changed (e.g., increased). Conversely, if the auto-exposure value threshold has recently (e.g., within the last few image frames) been decreased to account for a signal region size value that was too small, the determination made at operation 706 may instead be that the auto-exposure value threshold is still below the baseline auto-exposure value threshold and is to be gradually increased, such as back up to the baseline auto-exposure value threshold.

The baseline auto-exposure value threshold used at operation 706 may be a static, pre-calibrated threshold that is determined to be a desirable threshold when image frames depict ample signal content that is clearly distinguishable from background noise. For example, the baseline auto-exposure value threshold may be implemented as a pre-calibrated baseline auto-exposure value threshold that is determined when the one or more auto-exposure parameters used by the image capture system are set to one or more calibration parameters. In some implementations, the baseline auto-exposure value threshold may be calibrated offline (e.g., prior to operation) with a baseline set of auto-exposure parameters (e.g., the calibration parameters) that are configured to expose an image sensor of the image capture system for a particular exposure time (e.g., sixty frames per second (60 fps)) with a relatively bright illumination (e.g., full illumination of the illumination source of the image capture system) and standard gain parameters (e.g., a 1× analog gain, a 1× digital gain, etc.). Based on these calibration parameters, the baseline auto-exposure value threshold may be determined for use during system operation (e.g., when the auto-exposure parameters are set to different levels).

If the determination is made at operation 706 that the auto-exposure value threshold is less than the baseline auto-exposure value threshold ($V_{TH} < B_{TH}$), the control algorithm may lead to operation 708, where apparatus 100 may determine that the auto-exposure value threshold is to be changed (e.g., determining to increase the auto-exposure value threshold). In this example, even though the size of the signal region is large enough to exceed the signal region size threshold, the auto-exposure value threshold may still be small enough (e.g., likely due to previously being decremented at operation 512-1) to allow more noise than desirable to be included within the signal region. Accordingly, the control algorithm may be configured to attempt to eliminate some of that noise from the signal region (e.g., decreasing the size of the signal region), and flow is shown to proceed to operation 512-2, where apparatus 100 may increase (e.g., dynamically increase or increment) the auto-exposure value threshold based on the determining to increase the auto-exposure value threshold at operation 708. As such, when an additional frame (e.g., the subsequent frame) is later obtained, apparatus 100 may use the increased auto-exposure value threshold to perform the operations of flow diagram 500 for the additional frame. For example, apparatus 100 may identify, within the additional frame, a second signal region that includes pixels having auto-exposure values exceeding the increased auto-exposure value threshold (operation 504), and may determine, based on a size of the second signal region (operation 506), whether to further change the increased auto-exposure value threshold such as by further increasing the auto-exposure value threshold or decreasing the auto-exposure value threshold (operation 510).

As with the decreasing of the auto-exposure value threshold described above in relation to operation 512-1, apparatus 100 may perform the increasing of operation 512-2 1) in a stepwise manner in which a static incremental value is used to increment the auto-exposure value threshold each frame over a series of potentially several frames (the stepwise technique), 2) in a more instantaneous manner in which the auto-exposure value threshold is instantly changed back to the baseline auto-exposure value threshold or some other value below the baseline auto-exposure value threshold (the instantaneous technique), or 3) in some combination of the stepwise and instantaneous manners or in another suitable manner as may serve a particular implementation.

Returning to operation 706, if the determination is made that the auto-exposure value threshold is equal to the baseline auto-exposure value threshold ($V_{TH}=B_{TH}$) and does not need to be increased back up to this level, the control algorithm may lead to operation 710, where apparatus 100 determines that the auto-exposure value threshold is not to be changed (e.g., determining not to change the auto-exposure value threshold). In this example, the size of the signal region may be large enough to exceed the signal region size threshold, and the auto-exposure value threshold may already be set at the stable baseline auto-exposure value threshold at which signal content is properly accounted for and background noise largely ignored. Accordingly, the control algorithm may thus be configured to maintain the auto-exposure value threshold at the baseline rather than changing it, and flow is shown to proceed to operation 514, where, based on the determination at operation 710 that the auto-exposure value threshold is not to be changed, apparatus 100 controls the size of the signal region to remain at or above the signal region size threshold by maintaining the auto-exposure value threshold at the baseline auto-exposure value threshold.

It is noted that the operations shown in FIG. 7 generally ensure that the auto-exposure value threshold is either equal to or lower than the baseline auto-exposure value threshold, rather than ever being greater than the baseline auto-exposure value threshold. This is because the increasing of the auto-exposure value threshold at operation 512-2 might only be performed when operation 706 has determined that the auto-exposure value threshold is less than the baseline auto-exposure value threshold. As a result, FIG. 7 does not show a scenario in which a determination is made at operation 706 that the auto-exposure value threshold is greater than the baseline auto-exposure value threshold ($V_{TH}>B_{TH}$). It will be understood that, should such a situation somehow occur in certain implementations, apparatus 100 may be configured to gradually (e.g., in the stepwise manner) or instantly decrease the auto-exposure value threshold to be equal to (or at least no greater than) the baseline auto-exposure value threshold.

It will be understood that the changing (e.g., increasing and/or decreasing) of the auto-exposure value threshold at operations 512-1 and 512-2, as well as the maintaining of the auto-exposure value at operation 514, may be performed independently from and/or prior to any scaling of the auto-exposure value threshold that may be performed before the threshold is used for signal region identification purposes. For example, the scaling of the auto-exposure value threshold by the one or more gains (e.g., the analog gain and/or the bayer gain, etc.) mentioned above in connection with operations 602-606 may be performed regardless of whether the auto-exposure value threshold is changed or maintained in operations 512-514. As such, in certain implementations, the auto-exposure value threshold analyzed and processed by operations in FIG. 7 will be understood to be an unscaled (e.g., raw) version of the auto-exposure value threshold while the auto-exposure value threshold used for identifying the signal region in operations of FIG. 6 will be understood to be a scaled version of the auto-exposure value threshold (e.g., a version that is multiplied by the analog and/or bayer gains, as described above).

Returning to FIG. 5, operation 508 may be performed independently from (e.g., in parallel with) the performance of operations 506 and 510-514 before flow returns to operation 502 to obtain a subsequent image frame. At operation 508, one or more auto-exposure data points (e.g., auto-exposure values, auto-exposure targets, auto-exposure gains, etc.) may be determined for the image frame based on the signal region identified at operation 504. Based on these auto-exposure data points, apparatus 100 may adjust auto-exposure parameters of the image capture system in preparation for the image capture system capturing subsequent image frames in the image frame sequence. At operation 508, apparatus 100 may determine each auto-exposure data point based on captured data associated with the image frame obtained at operation 502 and based on the signal region identified at operation 504. For example, apparatus 100 may determine a frame auto-exposure value to be an average (e.g., a mean, median, mode, or other suitable average) of the auto-exposure values of the pixels identified (at operation 504) to be included within the signal region. Similarly, apparatus 100 may determine a frame auto-exposure target to be an average auto-exposure target for the pixels identified (at operation 504) to be included within the signal region.

Once the frame auto-exposure value and/or frame auto-exposure target have been determined, operation 508 may further include adjusting or otherwise updating (e.g., maintaining without an adjustment) the auto-exposure parameters of the image capture system being used to capture the image frame sequence. For example, based on a frame auto-exposure value and a frame auto-exposure target, apparatus 100 may determine a frame auto-exposure gain indicative of how much the auto-exposure parameters are to be adjusted to make the frame auto-exposure value better align with the frame auto-exposure target. The frame auto-exposure gain may then be used as a basis for adjusting (or maintaining) the auto-exposure parameters in any of the ways described herein.

Figure 8:
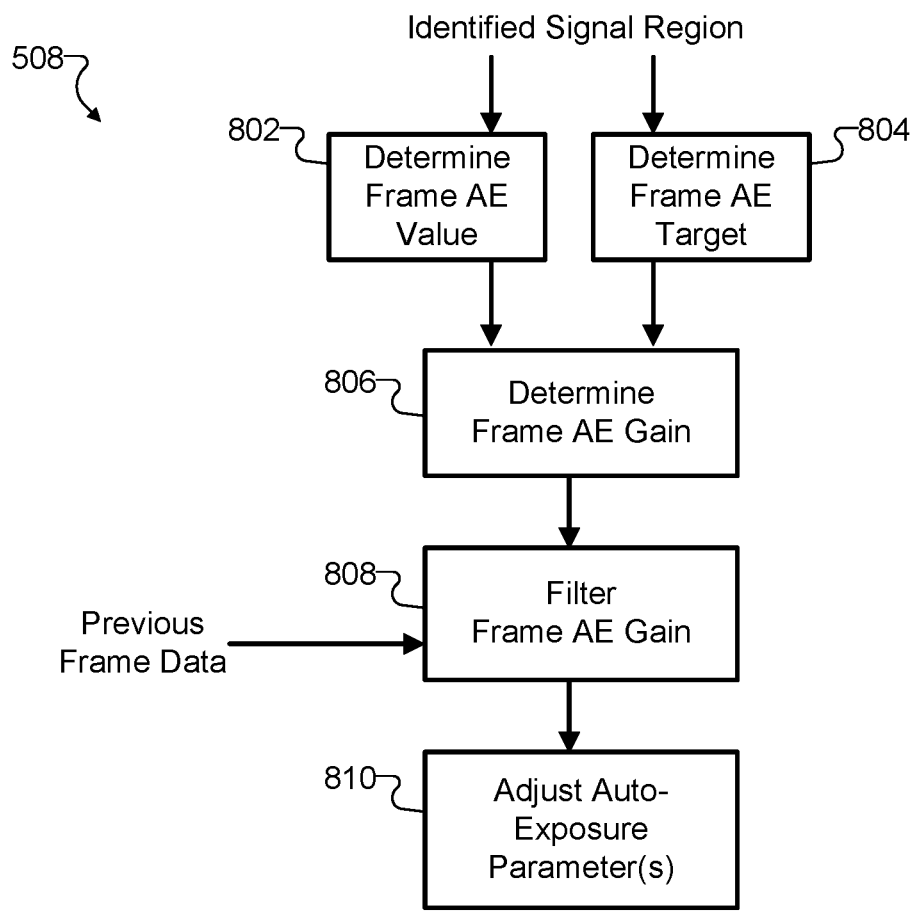
FIG. 8 shows an illustrative flow diagram for adjusting an auto-exposure parameter according to principles described herein.

FIG. 8 shows an illustrative flow diagram for adjusting an auto-exposure parameter at operation 508. As shown, apparatus 100 may determine a frame auto-exposure value at an operation 802 and may determine a frame auto-exposure target at an operation 804. As has been described, these operations may be performed based on (e.g., by averaging) auto-exposure values and/or auto-exposure targets for pixels or pixel groups identified to be included within a signal region of the image frame. Accordingly, as shown, data representative of the identified signal region (e.g., and data representative of pixel auto-exposure values and targets of the pixels included therein) may be used by apparatus 100 to perform operations 802 and 804.

Once the frame auto-exposure value and frame auto-exposure target are determined, apparatus 100 may perform an operation 806, which takes the frame auto-exposure value and frame auto-exposure target as inputs and uses them as a basis for determining a frame auto-exposure gain. The frame auto-exposure gain may be determined to correspond to a ratio of the frame auto-exposure target to the frame auto-exposure value. In this way, if the frame auto-exposure value is already equal to the frame auto-exposure target (e.g., such that no further adjustment is needed to align to the target), the frame auto-exposure gain may be set to a gain of 1, so that the system will neither try to boost nor attenuate the auto-exposure values for a subsequent frame that the image capture system captures. Conversely, if the frame auto-exposure target is different from the frame auto-exposure value, the frame auto-exposure gain may be set to correspond to a value less than or greater than 1 to cause the system to either boost or attenuate the auto-exposure values for the subsequent frame in an attempt to make the auto-exposure values more closely match the desired auto-exposure target.

At operation 808, the frame auto-exposure gain may be taken as an input along with other data (e.g., other frame auto-exposure gains) determined for previous image frames in the image frame sequence. Based on these inputs, operation 808 applies filtering to ensure that the auto-exposure gain does not change more quickly than desired and to thereby ensure that image frames presented to the user maintain a consistent brightness and change gradually. The filtering performed at operation 808 may be performed using a smoothing filter such as a temporal infinite impulse response (IIR) filter or another such digital or analog filter as may serve a particular implementation.

At operation 810, the filtered auto-exposure gain may be used as a basis for adjusting one or more auto-exposure parameters of the image capture system (e.g., for use by the image capture device or the fluorescence illumination source in capturing additional image frames). For example, as described above, adjusted auto-exposure parameters may include an exposure time parameter, a shutter aperture parameter, a luminance gain parameter, or the like. For image capture systems in which the illumination of the scene is largely or completely controlled by the image capture system (e.g., an image capture system including an endoscopic image capture device described above, an image capture system including a flash or other illumination source, etc.), adjusted auto-exposure parameters may further include an illumination intensity parameter, an illumination duration parameter, or the like.

Adjustments to the auto-exposure parameters of the image capture system may cause the image capture system to expose subsequent image frames in various different ways. For example, by adjusting the exposure time parameter, a shutter speed may be adjusted for a shutter included in the image capture system. For instance, the shutter may be held open for a longer period of time (e.g., to thereby increase the amount of exposure time of an image sensor) or for a shorter period of time (e.g., to thereby decrease the amount of exposure time for the image sensor). As another example, by adjusting the shutter aperture parameter, an aperture of the shutter may be adjusted to open more widely (e.g., to thereby increase the amount of light exposed to the image sensor) or less widely (e.g., to thereby decrease the amount of light exposed to the image sensor). As yet another example, by adjusting the luminance gain parameter, a sensitivity (e.g., an ISO sensitivity) may be increased or decreased to amplify or attenuate the illuminance as captured by the image capture system. For implementations in which the image capture system controls the illumination of the scene, the illumination intensity and/or illumination duration parameters may be adjusted to increase the intensity and duration of the light used to illuminate the scene being captured, thereby also affecting how much light the image sensor is exposed to.

Returning to FIG. 5, after the operations of flow diagram 500 have been performed, the current image frame may be considered fully processed by apparatus 100 and flow may return to operation 502, where a subsequent image frame of the image frame sequence may be obtained. The process may be repeated for the subsequent image frame and/or other subsequent image frames. It will be understood that, in certain examples, every image frame may be analyzed in accordance with flow diagram 500 to keep the auto-exposure value threshold, auto-exposure data points, and auto-exposure parameters as up-to-date as possible. In other examples, only certain image frames (e.g., every other image frame, every third image frame, etc.) may be so analyzed to conserve processing bandwidth in scenarios where more periodic auto-exposure processing still allows design specifications and targets to be achieved. It will also be understood that auto-exposure effects may tend to lag a few frames behind luminance changes at a scene, since auto-exposure parameter adjustments made based on one particular frame do not affect the exposure of that frame, but rather affect subsequent frames.

Based on any adjustments apparatus 100 makes to the auto-exposure parameters (and/or based on maintaining the auto-exposure parameters at their current levels when appropriate), apparatus 100 may successfully manage auto-exposure for image frames being captured by the image capture system, and subsequent image frames may be captured with desirable auto-exposure properties so as to have an attractive and beneficial appearance when presented to users.

Figure 9:
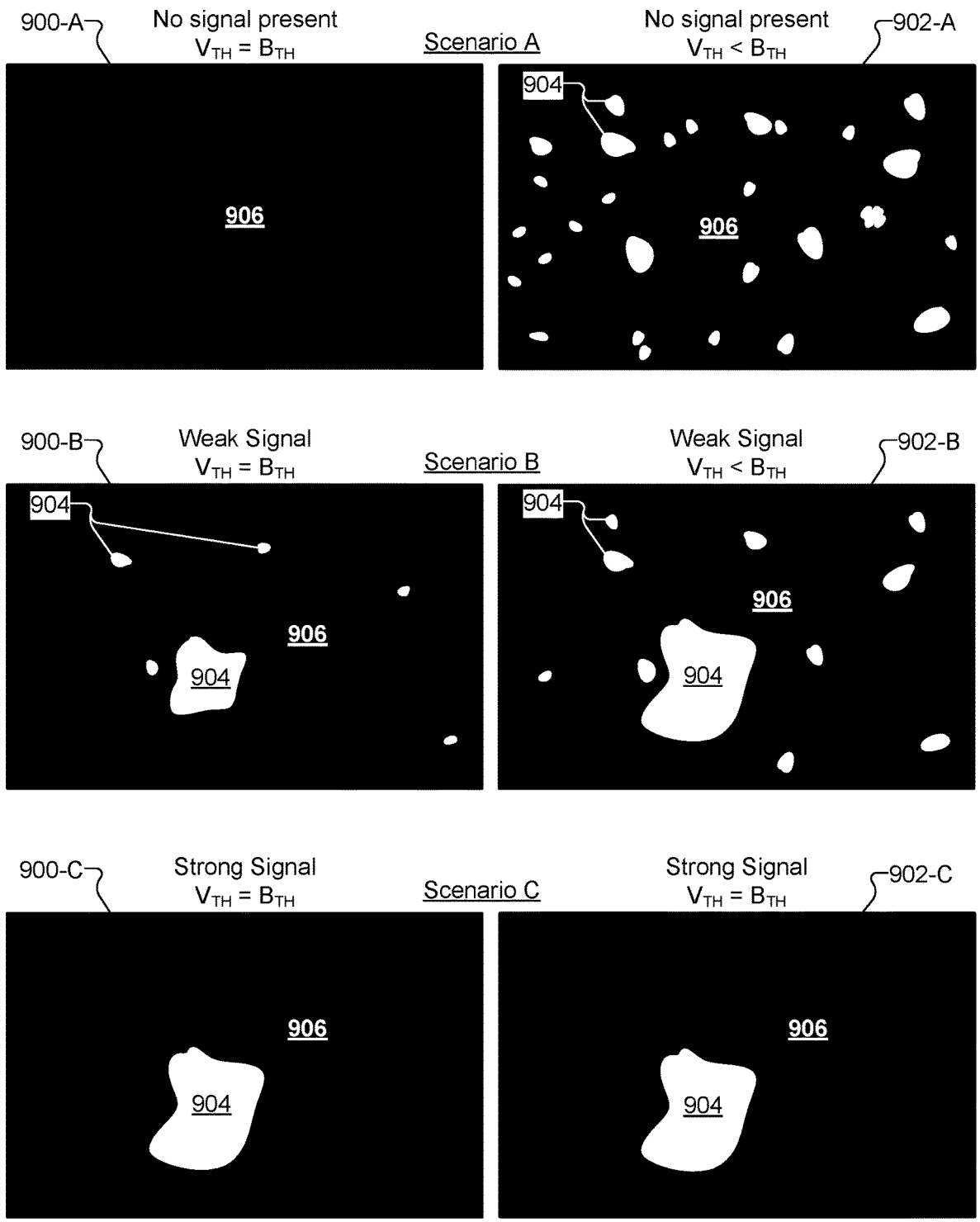
FIG. 9 shows illustrative effects of different auto-exposure value threshold settings on illustrative image frames depicting content with varying degrees of signal strength according to principles described herein.

To illustrate this, FIG. 9 shows examples of the effects that different auto-exposure value threshold settings may have on illustrative image frames depicting content with varying degrees of signal strength. On the top row of FIG. 9, illustrative image frames are shown for a first scenario (Scenario A) in which the signal content is extremely weak (e.g., the signal might be no brighter than background noise) or there is no signal content at all. Specifically, an image frame 900-A is shown on the left that illustrates Scenario A when the auto-exposure value threshold is set to the baseline auto-exposure value threshold. An image frame 902-A is shown on the right to illustrate the same scenario where the signal-region-size-based control is implemented so that the auto-exposure value threshold has been decreased to be less than the baseline auto-exposure value threshold.

In the middle row of FIG. 9, illustrative image frames are shown for a second scenario (Scenario B) in which signal content is present, but the signal content is weak (e.g., similar to background noise but, on average, at least a little brighter than the background noise). Specifically, an image frame 900-B is shown on the left that illustrates Scenario B when the auto-exposure value threshold is set to equal the baseline auto-exposure value threshold. An image frame 902-B is shown on the right to illustrate the same scenario where the signal-region-size-based control is implemented so that the auto-exposure value threshold has been decreased to be less than the baseline auto-exposure value threshold.

On the bottom row of FIG. 9, illustrative image frames are shown for a third scenario (Scenario C) in which signal content is present and is strong and/or pervasive enough that there is a relatively large signal region size including signal content that is distinguishable from the background noise. In this example, both an image frame 900-C shown on the left and an image frame 902-C shown on the right illustrate Scenario C when the auto-exposure value threshold is set to the baseline auto-exposure value threshold. This may be the case for scenario C because the signal-region-size-based control of the auto-exposure value threshold performed by auto-exposure management described herein may behave the same as auto-exposure management that does not implement signal-region-size-based control.

In each of image frames 900-A through 900-C and 902-A through 902-C, signal content and background noise bright enough to exceed the auto-exposure value threshold is depicted in white and is labeled as being included within a signal region 904 that will be accounted for in the adjustment of auto-exposure parameters described herein. Background content and background noise that does not exceed the auto-exposure value threshold is depicted in black and is labeled as being included within a background region 906 that will be ignored in the adjustment of auto-exposure parameters described herein. Accordingly, FIG. 9 illustrates how signal-region-size-controlled auto-exposure management described herein and illustrated by image frames 902 (in the right column of FIG. 9) may provide significant benefits, at least in certain scenarios, compared to auto-exposure management that is not based on signal region size and is illustrated by image frames 900 (in the left column of FIG. 9).

Scenario A may represent a scenario when there might not be anything for the user to see, regardless of how auto-exposure management is performed. For example, while image frame 900-A properly reflects that lack of signal content by showing a completely black image frame, it may be desirable for the user to see the brightest bits of background noise so that he or she can be assured that faint signal content is not being filtered out. Accordingly, image frame 902-A may show that the signal region may be identified in a manner that causes the auto-exposure parameter to be adjusted to see any content that may be present, even if it is no brighter than some background noise.

Scenario B may represent a scenario where signal-region-size-controlled auto-exposure management described herein may be beneficial. In Scenario B, there may be more actual signal content (e.g., the larger white shape) than can be identified with the auto-exposure value threshold set equal to the baseline auto-exposure value threshold. Accordingly, without a control mechanism that allows for the auto-exposure value threshold to be decreased below the baseline auto-exposure value threshold, the identified signal region might exclude some of the actual signal content, and the auto-exposure management might not properly account for more (e.g., all) of the signal content. The already faint signal content may be even more difficult for the user to see in these scenarios (e.g., as shown in image frame 900-B). By decreasing the auto-exposure value threshold below the baseline auto-exposure value threshold in accordance with principles described herein, image frame 902-B may show more of the signal content (e.g., an entirety of the signal content), albeit possibly with slightly more background noise.

Scenario C may represent a scenario where there is not a concern that signal content will be conflated with background noise. In this scenario, the signal-region-size-controlled auto-exposure value threshold may max out at the baseline auto-exposure value threshold such that the auto-exposure management of image frame 902-C is identical to that of image frame 900-C.

As has been described, apparatus 100, method 200, and/or system 300 may each be associated in certain examples with a computer-assisted medical system used to perform a medical procedure (e.g., a fluorescence-guided surgical procedure, a fluorescence-guided research experiment, etc.) on a body. To illustrate, FIG. 10 shows an illustrative computer-assisted medical system 1000 that may be used to perform various types of medical procedures including surgical and/or non-surgical procedures.

Figure 10:
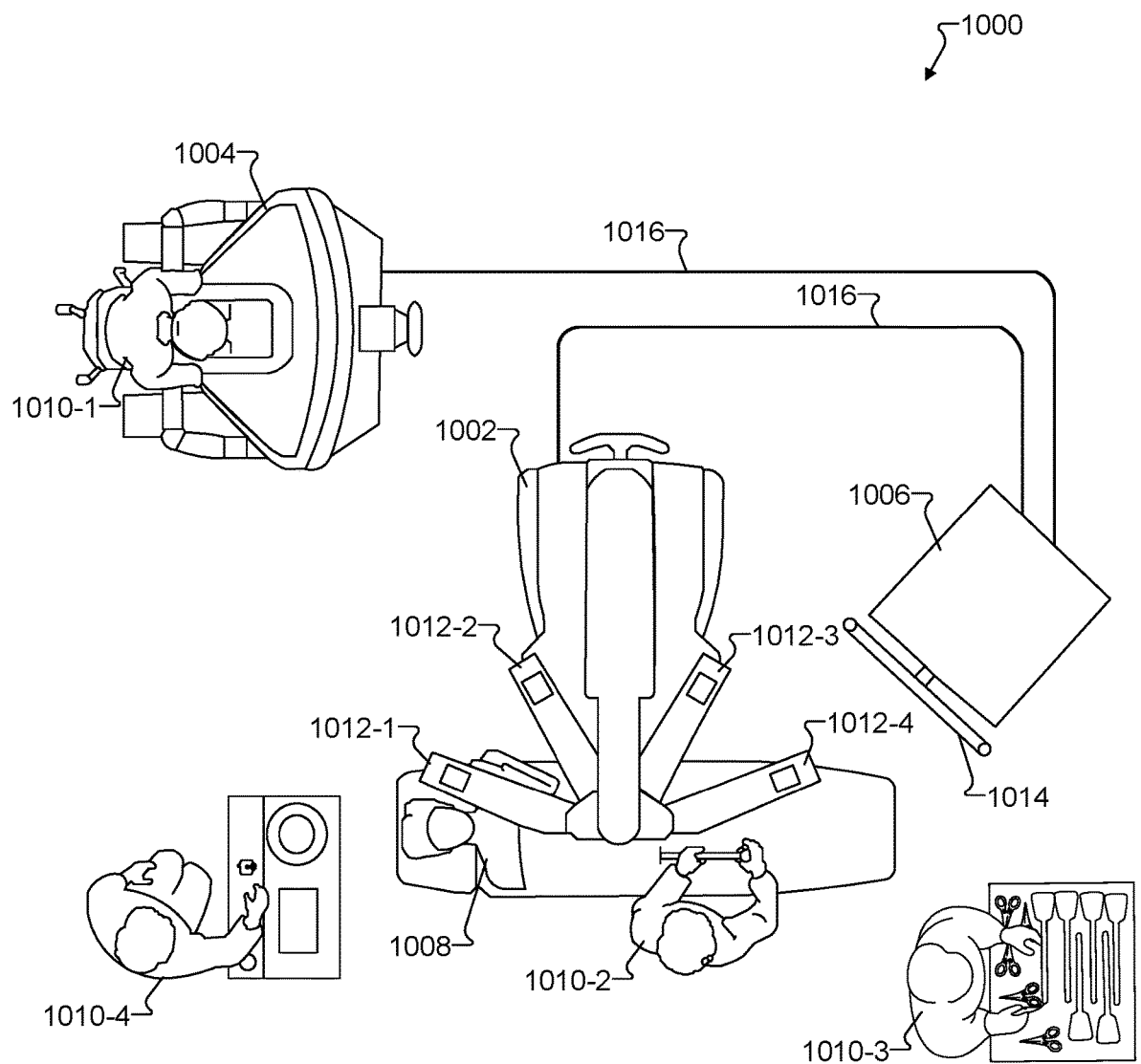
FIG. 10 shows an illustrative computer-assisted medical system according to principles described herein.

As shown, computer-assisted medical system 1000 may include a manipulator assembly 1002 (a manipulator cart is shown in FIG. 10), a user control apparatus 1004, and an auxiliary apparatus 1006, all of which are communicatively coupled to each other. Computer-assisted medical system 1000 may be utilized by a medical team to perform a computer-assisted medical procedure or other similar operation on a body of a patient 1008 or on any other body as may serve a particular implementation. As shown, the medical team may include a first user 1010-1 (such as a surgeon for a surgical procedure), a second user 1010-2 (such as a patient-side assistant), a third user 1010-3 (such as another assistant, a nurse, a trainee, etc.), and a fourth user 1010-4 (such as an anesthesiologist for a surgical procedure), all of whom may be collectively referred to as users 1010, and each of whom may control, interact with, or otherwise be a user of computer-assisted medical system 1000. More, fewer, or alternative users may be present during a medical procedure as may serve a particular implementation. For example, team composition for different medical procedures, or for non-medical procedures, may differ and include users with different roles.

While FIG. 10 illustrates an ongoing minimally invasive medical procedure such as a minimally invasive surgical procedure, it will be understood that computer-assisted medical system 1000 may similarly be used to perform open medical procedures or other types of operations. For example, operations such as exploratory imaging operations, mock medical procedures used for training purposes, research experiments (e.g., molecular biomedical research experiments), and/or other operations may also be performed.

As shown in FIG. 10, manipulator assembly 1002 may include one or more manipulator arms 1012 (e.g., manipulator arms 1012-1 through 1012-4) to which one or more instruments may be coupled. The instruments may be used for a computer-assisted medical procedure on patient 1008 (e.g., in a surgical example, by being at least partially inserted into patient 1008 and manipulated within patient 1008). While manipulator assembly 1002 is depicted and described herein as including four manipulator arms 1012, it will be recognized that manipulator assembly 1002 may include a single manipulator arm 1012 or any other number of manipulator arms as may serve a particular implementation. While the example of FIG. 10 illustrates manipulator arms 1012 as being robotic manipulator arms, it will be understood that, in some examples, one or more instruments may be partially or entirely manually controlled, such as by being handheld and controlled manually by a person. For instance, these partially or entirely manually controlled instruments may be used in conjunction with, or as an alternative to, computer-assisted instrumentation that is coupled to manipulator arms 1012 shown in FIG. 10.

During the medical operation, user control apparatus 1004 may be configured to facilitate teleoperational control by user 1010-1 of manipulator arms 1012 and instruments attached to manipulator arms 1012. To this end, user control apparatus 1004 may provide user 1010-1 with imagery of an operational area associated with patient 1008 as captured by an imaging device. To facilitate control of instruments, user control apparatus 1004 may include a set of master controls. These master controls may be manipulated by user 1010-1 to control movement of the manipulator arms 1012 or any instruments coupled to manipulator arms 1012.

Auxiliary apparatus 1006 may include one or more computing devices configured to perform auxiliary functions in support of the medical procedure, such as providing insufflation, electrocautery energy, illumination or other energy for imaging devices, image processing, or coordinating components of computer-assisted medical system 1000. In some examples, auxiliary apparatus 1006 may be configured with a display monitor 1014 configured to display one or more user interfaces, or graphical or textual information in support of the medical procedure. In some instances, display monitor 1014 may be implemented by a touchscreen display and provide user input functionality. Augmented content provided by a region-based augmentation system may be similar, or differ from, content associated with display monitor 1014 or one or more display devices in the operation area (not shown).

As will be described in more detail below, apparatus 100 may be implemented within or may operate in conjunction with computer-assisted medical system 1000. For instance, in certain implementations, apparatus 100 may be implemented by computing resources included within an instrument (e.g., an endoscopic or other imaging instrument) attached to one of manipulator arms 1012, or by computing resources associated with manipulator assembly 1002, user control apparatus 1004, auxiliary apparatus 1006, or another system component not explicitly shown in FIG. 10.

Manipulator assembly 1002, user control apparatus 1004, and auxiliary apparatus 1006 may be communicatively coupled one to another in any suitable manner. For example, as shown in FIG. 10, manipulator assembly 1002, user control apparatus 1004, and auxiliary apparatus 1006 may be communicatively coupled by way of control lines 1016, which may represent any wired or wireless communication link as may serve a particular implementation. To this end, manipulator assembly 1002, user control apparatus 1004, and auxiliary apparatus 1006 may each include one or more wired or wireless communication interfaces, such as one or more local area network interfaces, Wi-Fi network interfaces, cellular interfaces, and so forth.

In certain embodiments, one or more of the processes described herein may be implemented at least in part as instructions embodied in a non-transitory computer-readable medium and executable by one or more computing devices. In general, a processor (e.g., a microprocessor) receives instructions, from a non-transitory computer-readable medium, (e.g., a memory, etc.), and executes those instructions, thereby performing one or more processes, including one or more of the processes described herein. Such instructions may be stored and/or transmitted using any of a variety of known computer-readable media.

A computer-readable medium (also referred to as a processor-readable medium) includes any non-transitory medium that participates in providing data (e.g., instructions) that may be read by a computer (e.g., by a processor of a computer). Such a medium may take many forms, including, but not limited to, non-volatile media, and/or volatile media. Non-volatile media may include, for example, optical or magnetic disks and other persistent memory. Volatile media may include, for example, dynamic random access memory (DRAM), which typically constitutes a main memory. Common forms of computer-readable media include, for example, a disk, hard disk, magnetic tape, any other magnetic medium, a compact disc read-only memory (CD-ROM), a digital video disc (DVD), any other optical medium, random access memory (RAM), programmable read-only memory (PROM), electrically erasable programmable read-only memory (EPROM), FLASH-EEPROM, any other memory chip or cartridge, or any other tangible medium from which a computer can read.

Figure 11:
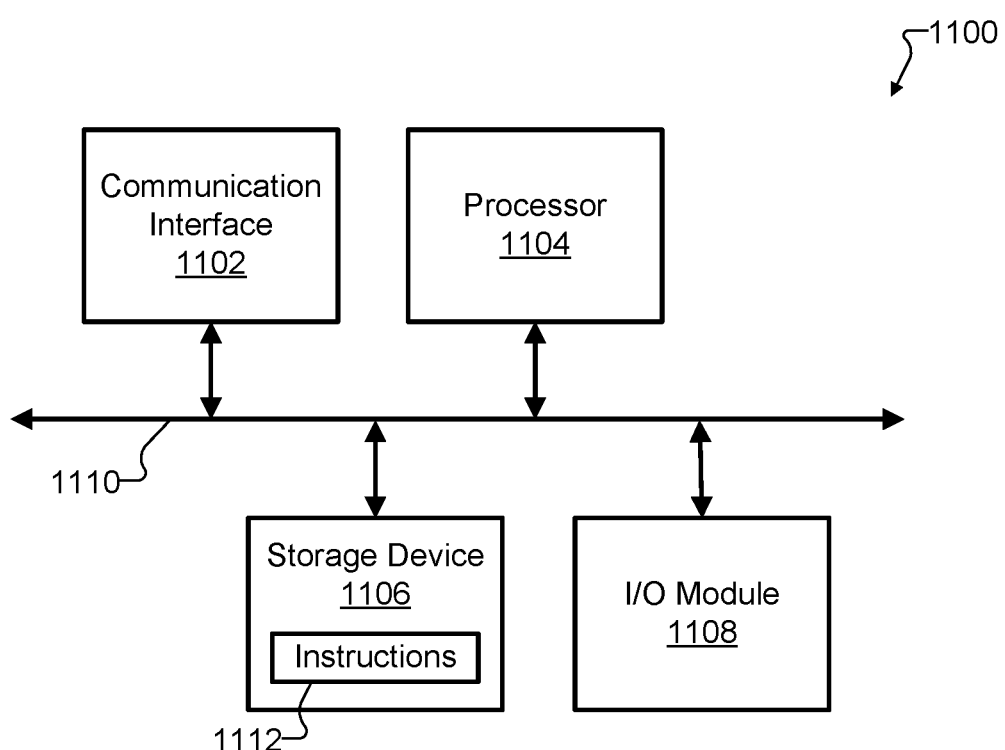
FIG. 11 shows an illustrative computing system according to principles described herein.

FIG. 11 shows an illustrative computing system 1100 that may be specifically configured to perform one or more of the processes described herein. For example, computing system 1100 may include or implement (or partially implement) an auto-exposure management apparatus such as apparatus 100, an auto-exposure management system such as system 300, or any other computing systems or devices described herein.

As shown in FIG. 11, computing system 1100 may include a communication interface 1102, a processor 1104, a storage device 1106, and an input/output ("I/O") module 1108 communicatively connected via a communication infrastructure 1110. While an illustrative computing system 1100 is shown in FIG. 11, the components illustrated in FIG. 11 are not intended to be limiting. Additional or alternative components may be used in other embodiments. Components of computing system 1100 shown in FIG. 11 will now be described in additional detail.

Communication interface 1102 may be configured to communicate with one or more computing devices. Examples of communication interface 1102 include, without limitation, a wired network interface (such as a network interface card), a wireless network interface (such as a wireless network interface card), a modem, an audio/video connection, and any other suitable interface.

Processor 1104 generally represents any type or form of processing unit capable of processing data or interpreting, executing, and/or directing execution of one or more of the instructions, processes, and/or operations described herein. Processor 1104 may direct execution of operations in accordance with one or more applications 1112 or other computer-executable instructions such as may be stored in storage device 1106 or another computer-readable medium.

Storage device 1106 may include one or more data storage media, devices, or configurations and may employ any type, form, and combination of data storage media and/or device. For example, storage device 1106 may include, but is not limited to, a hard drive, network drive, flash drive, magnetic disc, optical disc, RAM, dynamic RAM, other non-volatile and/or volatile data storage units, or a combination or sub-combination thereof. Electronic data, including data described herein, may be temporarily and/or permanently stored in storage device 1106. For example, data representative of one or more executable applications 1112 configured to direct processor 1104 to perform any of the operations described herein may be stored within storage device 1106. In some examples, data may be arranged in one or more databases residing within storage device 1106.

I/O module 1108 may include one or more I/O modules configured to receive user input and provide user output. One or more I/O modules may be used to receive input for a single virtual experience. I/O module 1108 may include any hardware, firmware, software, or combination thereof supportive of input and output capabilities. For example, I/O module 1108 may include hardware and/or software for capturing user input, including, but not limited to, a keyboard or keypad, a touchscreen component (e.g., touchscreen display), a receiver (e.g., an RF or infrared receiver), motion sensors, and/or one or more input buttons.

I/O module 1108 may include one or more devices for presenting output to a user, including, but not limited to, a graphics engine, a display (e.g., a display screen), one or more output drivers (e.g., display drivers), one or more audio speakers, and one or more audio drivers. In certain embodiments, I/O module 1108 is configured to provide graphical data to a display for presentation to a user. The graphical data may be representative of one or more graphical user interfaces and/or any other graphical content as may serve a particular implementation.

In some examples, any of the facilities described herein may be implemented by or within one or more components of computing system 1100. For example, one or more applications 1112 residing within storage device 1106 may be configured to direct processor 1104 to perform one or more processes or functions associated with processor 104 of apparatus 100. Likewise, memory 102 of apparatus 100 may be implemented by or within storage device 1106.

In the preceding description, various illustrative embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. An apparatus comprising:
   one or more processors; and
   memory storing executable instructions that, when executed by the one or more processors, cause the apparatus to:
   identify, within a first image frame captured by an image capture system, a first signal region that includes pixels having auto-exposure values exceeding a first auto-exposure value threshold;
   adjust, based on the auto-exposure values of the pixels included within the first signal region, one or more auto-exposure parameters used by the image capture system to capture a second image frame;
   change, based on a size of the first signal region, the first auto-exposure value threshold to a second auto-exposure value threshold;
   identify, within the second image frame, a second signal region that include pixels having auto-exposure values exceeding the second auto-exposure value threshold; and
   adjust, based on the auto-exposure values of the pixels included with the second signal region, one or more auto-exposure parameters used by the image capture system to capture a third image frame.

2. The apparatus of claim 1, wherein the instructions, when executed by the one or more processors, further cause the apparatus to:
   determine that the size of the first signal region is less than a signal region size threshold;
   wherein the changing the first auto-exposure value threshold to the second auto-exposure value threshold is performed based on the determining that the size of the first signal region is less than a signal region size threshold and comprises decreasing the first auto-exposure value threshold to the second auto-exposure value threshold.

3. The apparatus of claim 1, wherein the instructions, when executed by the one or more processors, further cause the apparatus to:
   determine that the size of the first signal region is at or above a signal region size threshold, and
   determine that the first auto-exposure value threshold is less than a baseline auto-exposure value threshold;
   wherein the changing the first auto-exposure value threshold to the second auto-exposure value threshold is performed based on the determining that the size of the first signal region is at or above the signal region size threshold and the determining that the first auto-exposure value threshold is less than a baseline auto-exposure value threshold, and
   wherein the changing the first auto-exposure value threshold to the second auto-exposure value threshold comprises increasing the first auto-exposure value threshold to the second auto-exposure value threshold.

4. The apparatus of claim 1, wherein the changing the first auto-exposure value threshold to the second auto-exposure value threshold is performed based on a pre-calibrated baseline auto-exposure value threshold that is determined when the one or more auto-exposure parameters used by the image capture system are set to one or more calibration parameters.

5. The apparatus of claim 1, wherein:
   the image capture system includes an endoscopic image capture device configured to capture the first image frame as part of an image frame sequence that depicts a view of a body undergoing a fluorescence-guided medical procedure;
   the first image frame depicts fluorescence content against a darkened background, the fluorescence content generated by a fluorescence imaging agent that fluoresces when illuminated by a fluorescence illumination source; and
   the first signal region identified within the first image frame corresponds to the fluorescence content.

6. The apparatus of claim 5, wherein the fluorescence imaging agent is diluted such that at least a portion of the fluorescence content is associated with an auto-exposure value less than an auto-exposure value associated with at least a portion of noise within the first image frame.

7. The apparatus of claim 1, wherein:
   the instructions, when executed by the one or more processors, cause the apparatus to:
   determine, based on the auto-exposure values of the pixels included within the first signal region, a frame auto-exposure value and a frame auto-exposure target, and
   determine, based on the frame auto-exposure value and the frame auto-exposure target, a frame auto-exposure gain; and the adjusting the one or more auto-exposure parameters includes adjusting the one or more auto-exposure parameters based on the frame auto-exposure gain.

8. The apparatus of claim 7, wherein:
the instructions, when executed by the one or more processors, cause the apparatus to filter, using a smoothing filter and based on one or more frame auto-exposure parameter gains associated with one or more frames in an image frame sequence that includes the first image frame, the frame auto-exposure gain; and
the adjusting the one or more auto-exposure parameters is based on the filtered frame auto-exposure gain.

9. The apparatus of claim 1, wherein the one or more auto-exposure parameters include one or more of:
an exposure time parameter;
a shutter aperture parameter;
an illumination intensity parameter; or
a luminance gain parameter.

10. A system comprising:
a fluorescence illumination source configured to illuminate tissue that includes a fluorescence imaging agent that fluoresces when illuminated by the fluorescence illumination source;
an image capture device configured to capture an image frame sequence that includes a first image frame depicting the tissue as illuminated by the fluorescence illumination source; and
one or more processors configured to:
identify, within the first image frame captured by the image capture device, a first signal region that includes pixels having auto-exposure values exceeding a first auto-exposure value threshold;
adjust, based on the auto-exposure values of the pixels included within the first signal region, one or more auto-exposure parameters used by the image capture device or the fluorescence illumination source to capture a second image frame of the image frame sequence;
change, based on a size of the first signal region, the first auto-exposure value threshold to a second auto-exposure value threshold;
identify, within the second image frame, a second signal region that include pixels having auto-exposure values exceeding the second auto-exposure value threshold; and
adjust, based on the auto-exposure values of the pixels included with the second signal region, one or more auto-exposure parameters used by the image capture system to capture a third image frame.

11. The system of claim 10, wherein the changing the first auto-exposure value threshold to the second auto-exposure value threshold comprises decreasing the first auto-exposure value threshold to the second auto-exposure value threshold.

12. The system of claim 10, wherein the changing the first auto-exposure value threshold to the second auto-exposure value threshold comprises increasing the first auto-exposure value threshold to the second auto-exposure value threshold.

13. A method comprising:
identifying, by a computing device within a first image frame captured by an image capture system, a first signal region that includes pixels having auto-exposure values exceeding a first auto-exposure value threshold;
adjusting, by the computing device based on the auto-exposure values of the pixels included within the first signal region, one or more auto-exposure parameters used by the image capture system to capture a second image frame;
changing, by the computing device based on a size of the first signal region, the first auto-exposure value threshold to a second auto-exposure value threshold;
identifying, by the computing device within the second image frame, a second signal region that include pixels having auto-exposure values exceeding the second auto-exposure value threshold; and
adjusting, by the computing device based on the auto-exposure values of the pixels included with the second signal region, one or more auto-exposure parameters used by the image capture system to capture a third image frame.

14. The method of claim 13, wherein the method further comprises:
determining, by the computing device, that the size of the first signal region is less than a signal region size threshold;
wherein the changing the first auto-exposure value threshold to the second auto-exposure value threshold is performed based on the determining that the size of the first signal region is less than a signal region size threshold and comprises decreasing the first auto-exposure value threshold to the second auto-exposure value threshold.

15. The method of claim 13, wherein the method further comprises:
determining, by the computing device, that the size of the first signal region is at or above a signal region size threshold, and
determining, by the computing device, that the first auto-exposure value threshold is less than a baseline auto-exposure value threshold;
wherein the changing the first auto-exposure value threshold to the second auto-exposure value threshold is performed based on the determining that the size of the first signal region is at or above the signal region size threshold and the determining that the first auto-exposure value threshold is less than a baseline auto-exposure value threshold, and
wherein the changing the first auto-exposure value threshold to the second auto-exposure value threshold comprises increasing the first auto-exposure value threshold to the second auto-exposure value threshold.

16. The method of claim 13, wherein the changing the first auto-exposure value threshold to the second auto-exposure value threshold is performed based on a pre-calibrated baseline auto-exposure value threshold that is determined when the one or more auto-exposure parameters used by the image capture system are set to one or more calibration parameters.

17. The method of claim 13, wherein:
the image capture system includes an endoscopic image capture device configured to capture the first image frame as part of an image frame sequence that depicts a view of a body undergoing a fluorescence-guided medical procedure;
the first image frame depicts fluorescence content against a darkened background, the fluorescence content generated by a fluorescence imaging agent that fluoresces when illuminated by a fluorescence illumination source; and
the first signal region identified within the first image frame corresponds to the fluorescence content.

18. The method of claim 17, wherein the fluorescence imaging agent is diluted such that at least a portion of the fluorescence content is associated with an auto-exposure value less than an auto-exposure value associated with at least a portion of noise within the first image frame.

19. The method of claim 13, further comprising:
   determining, by the computing device based on the auto-exposure values of the pixels included within the first signal region, a frame auto-exposure value and a frame auto-exposure target; and
   determining, based on the frame auto-exposure value and the frame auto-exposure target, a frame auto-exposure gain;
   wherein the adjusting the one or more auto-exposure parameters includes adjusting the one or more auto-exposure parameters based on the frame auto-exposure gain.

20. The method of claim 13, wherein the one or more auto-exposure parameters include one or more of:
   an exposure time parameter;
   a shutter aperture parameter;
   an illumination intensity parameter; or
   a luminance gain parameter.

\* \* \* \* \*